United States Patent
Mimura et al.

(10) Patent No.: US 9,384,550 B2
(45) Date of Patent: Jul. 5, 2016

(54) IMAGE PROCESSING DEVICE AND STORAGE MEDIUM FOR IMAGE PROCESSING

(71) Applicant: Konica Minolta, Inc., Tokyo (JP)

(72) Inventors: Yusuke Mimura, Hino (JP); Osamu Toyama, Kakogawa (JP)

(73) Assignee: KONICA MINOLTA, INC., Tokyo (JP)

(*) Notice: Subject to any disclaimer, the term of this patent is extended or adjusted under 35 U.S.C. 154(b) by 0 days.

(21) Appl. No.: 14/902,214

(22) PCT Filed: Mar. 27, 2014

(86) PCT No.: PCT/JP2014/058721
§ 371 (c)(1),
(2) Date: Dec. 30, 2015

(87) PCT Pub. No.: WO2015/145643
PCT Pub. Date: Oct. 1, 2015

(65) Prior Publication Data
US 2016/0163043 A1 Jun. 9, 2016

(51) Int. Cl.
*G06K 9/00* (2006.01)
*G06T 7/00* (2006.01)
*G06T 7/60* (2006.01)
*G01N 33/483* (2006.01)

(52) U.S. Cl.
CPC .......... *G06T 7/0012* (2013.01); *G01N 33/4833* (2013.01); *G06T 7/0081* (2013.01); *G06T 7/0085* (2013.01); *G06T 7/60* (2013.01); *G06T 2207/30024* (2013.01)

(58) Field of Classification Search
None
See application file for complete search history.

(56) References Cited

U.S. PATENT DOCUMENTS

| | | | | |
|---|---|---|---|---|
| 2002/0186874 A1* | 12/2002 | Price | ............... | G01N 15/147 382/133 |
| 2006/0013455 A1* | 1/2006 | Watson | ............... | G06K 9/0014 382/128 |
| 2006/0039593 A1* | 2/2006 | Sammak | ............ | G06K 9/00127 382/133 |
| 2006/0127881 A1* | 6/2006 | Wong | ................ | G06K 9/00127 435/4 |
| 2009/0169090 A1* | 7/2009 | Griffin | ............... | G06K 9/00127 382/133 |

FOREIGN PATENT DOCUMENTS

| | | |
|---|---|---|
| JP | 2000321031 A | 11/2000 |
| JP | 2000331143 A | 11/2000 |
| JP | 2011186750 A | 9/2011 |
| JP | 2012037432 A | 2/2012 |
| JP | 2013020212 A | 1/2013 |
| WO | 2013146843 A1 | 10/2013 |

OTHER PUBLICATIONS

International Search Report dated Jul. 1, 2014 for Application No. PCT/JP2014/058721 and English translation.
PCT/ISA/237 and partial English translation.
Office action mailed Apr. 7, 2015 for corresponding Japanese Application No. 2015-506956.

* cited by examiner

*Primary Examiner* — Hadi Akhavannik
(74) *Attorney, Agent, or Firm* — Lucas & Mercanti, LLP

(57) ABSTRACT

An image processing device extracts a candidate region and region information of the cell nucleus from a cell image (S20), judges whether or not to correct the candidate region of the cell nucleus on the basis of the region information of the cell nucleus, and corrects the candidate region of the cell nucleus on the basis of the judged result (S40).

6 Claims, 28 Drawing Sheets

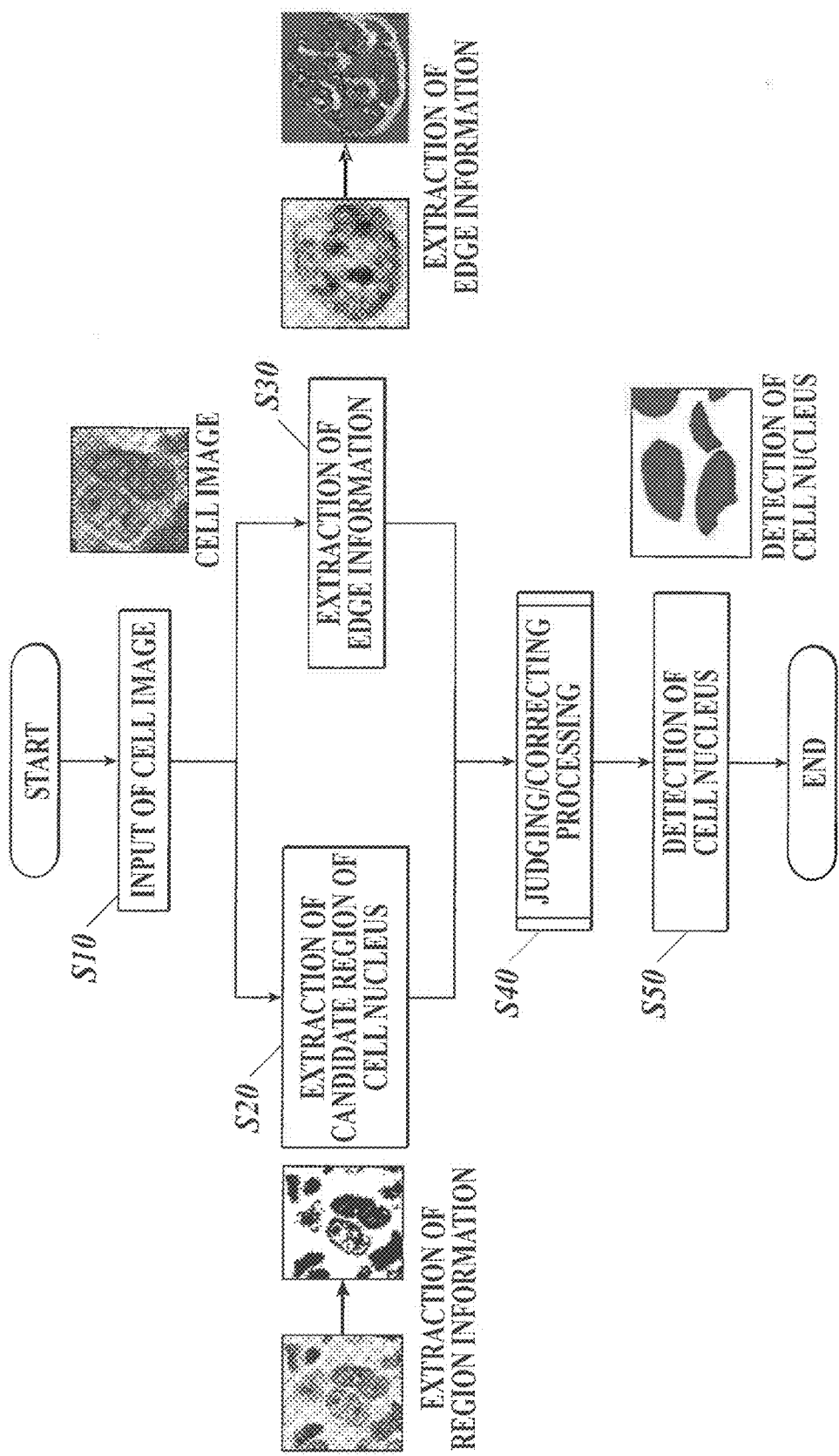

FIG. 5

| FORM OF CELL NUCLEUS | CELL IMAGE | BINARY IMAGE | EDGE INTENSITY | EDGE ANGLE | NORMAL LINE DIRECTION OF AN EDGE |
|---|---|---|---|---|---|
| CLEAR | 30 | | | | |
| SCATTERED | 40 | | | | |
| CONTIGUOUS | 50 | | | | |

EDGE INTENSITY IMAGE

IMAGE OF NORMAL LINE DIRECTION OF AN EDGE

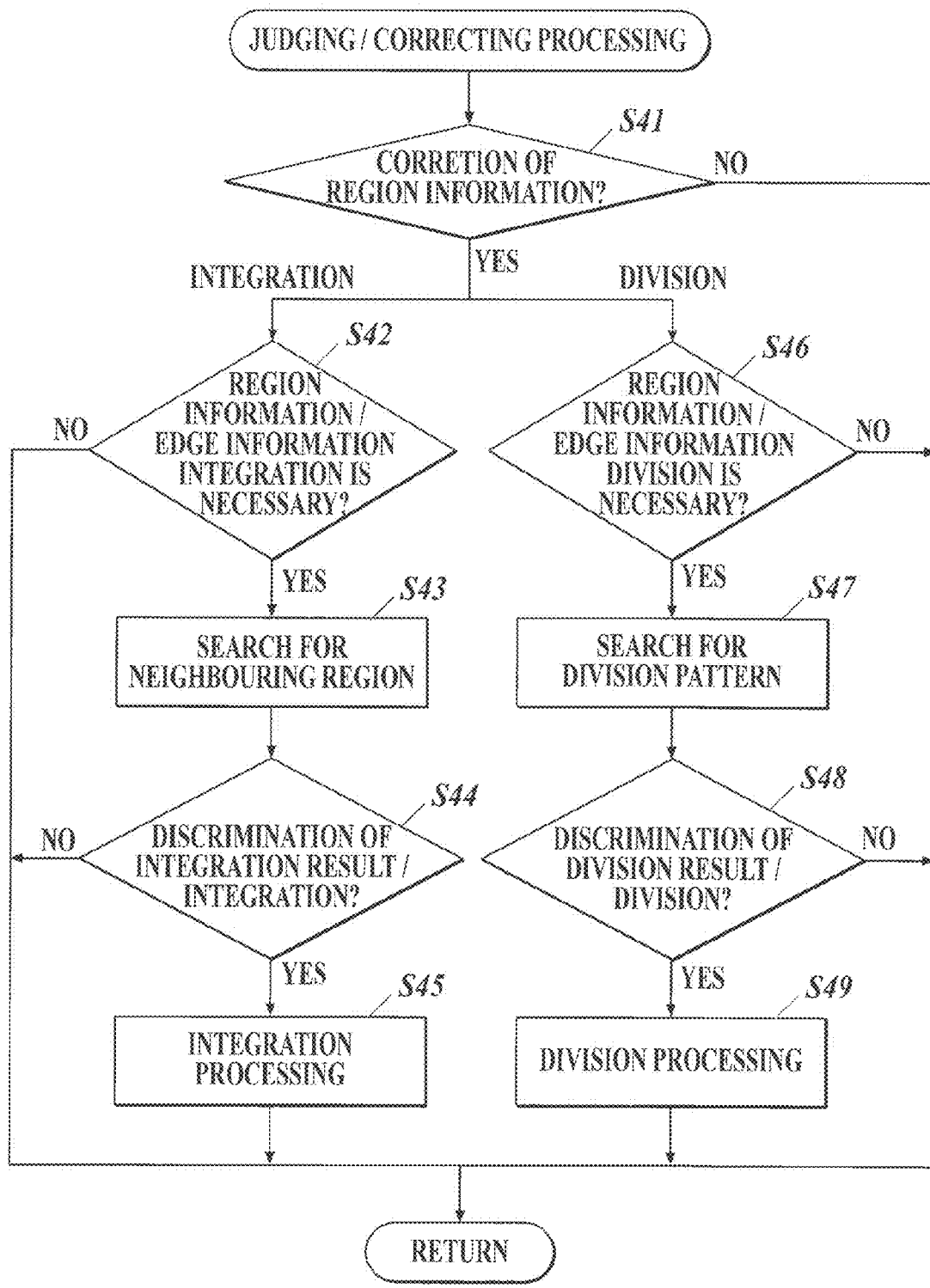

FIG.20A
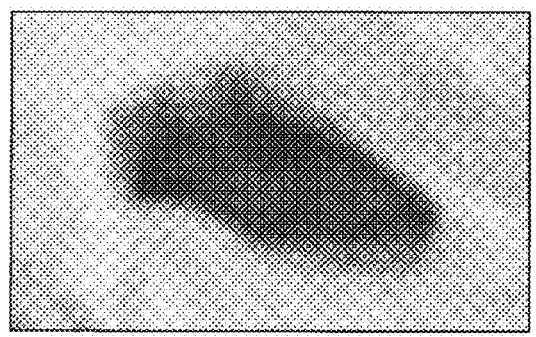
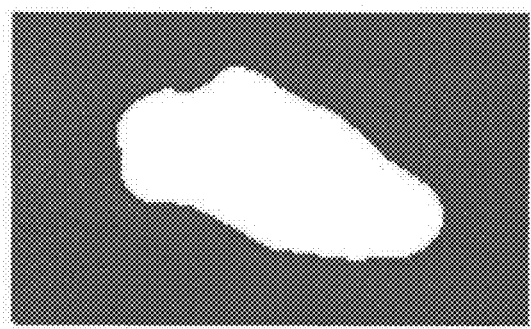

FIG.20B
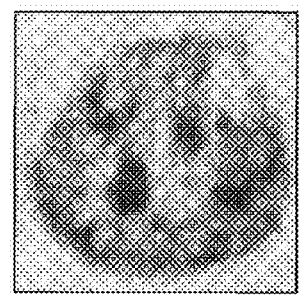
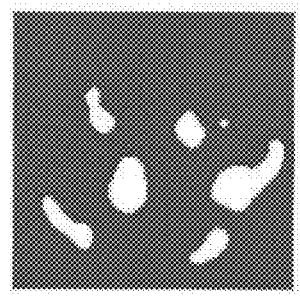

*FIG.20C*
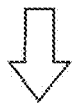
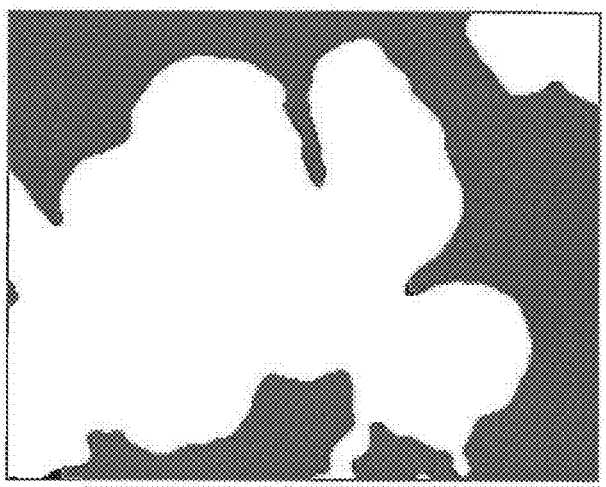

IMAGE PROCESSING DEVICE AND STORAGE MEDIUM FOR IMAGE PROCESSING

CROSS REFERENCE TO RELATED APPLICATION

This application is a 371 of PCT/JP2014/058721 filed on Mar. 27, 2014, application which is incorporated herein by reference.

TECHNICAL FIELD

The present invention relates to an image processing device and an image processing program, and specifically relates to image processing for pathological diagnosis.

BACKGROUND ART

A diagnosis of the presence of a lesion or the kind of a lesion by observing a tissue slice obtained from a human body with a microscope, so called a pathological diagnosis, has been actively performed. A tissue sample which is a target of pathological diagnosis is generally prepared so as to suit microscopic observation, through a fixation process, embedding process, slicing process, and staining process. In many techniques suggested in recent years, a high-magnification image data (a cell image) of a stained tissue slice has been generated using a microscope and image processing has been performed for the cell image in order to extract objects (such as cell nuclei) exactly.

For example, according to the technique described in Patent Document 1, the shapes of individual cells are intended to be extracted even when a plurality of cells overlap with each other on the cell image (see paragraph 0018). In this technique, specifically by focusing on the dyeing concentration (concentration gradient) of cells, the shapes of individual cells are intended to be extracted on the basis of positive or negative codes of an inner product value of a concentration gradient vector at a pixel constituting the outline of a cell and a displacement vector from the pixel to the center of the cell (see paragraphs 0027 to 0028, FIG. 10, paragraphs 0084 to 0088, FIGS. 13 to 16).

According to the technique described in Patent Document 2, effects of noises and edges of other tissues are intended to be removed in extracting the shapes of objects (cell nuclei) from a cell image (see paragraphs 0014 to 0015). Specifically, this technique is realized by a publically-known SNAKES processing performed to a blurred image and a non-blurred image (see paragraphs 0037-0039, FIG. 1, etc.), by a processing to paint a blank portion in a cell nucleus using the color around the blank portion in advance when there is a blank portion in the cell nucleus in the cell image (see paragraphs 0044 to 0046, FIG. 3, etc.), etc.

PRIOR ART LITERATURES

Patent Literature

Patent Document 1: Japanese Patent Application Publication No. 2000-321031

Patent Document 1: Japanese Patent Application Publication No. 2000-331143

SUMMARY OF INVENTION

Problems to Be Solved By the Invention

Although staining of a tissue slice is conducted in order to easily detect the shapes of an object, such as a cell nucleus, a cell nucleus is not always stained clearly. Especially, an advanced cancer cell is often stained unevenly.

That is, a single cell nucleus can be detected from a cell image obtained from a clearly-stained cell nucleus as shown in FIG. 20A. Meanwhile, by image processing of a cell image of an advanced cancer cell, a single cell nucleus may be sparsely detected and results in incorrect detection of the single cell nucleus as a plurality of cell nuclei (see FIG. 20B). On the contrary, a plurality of cell nuclei may be incorrectly detected as a single cell nucleus, when a plurality of cell nuclei are contiguous with each other.

Given the above, a main object of the present invention is to provide an image processing device and an image processing program capable of detecting an individual cell nucleus without incorrectly detecting a single cell nucleus as a plurality of cell nuclei, even when the cell nucleus is not stained uniformly or is contiguous with neighboring cell nuclei.

Means for Solving Problems

According to an aspect of the present invention for solving the above-described problems, there is provided an image processing device for detecting a cell nucleus in a cell image in which the cell nucleus is stained, including:

a region-extracting unit to extract a candidate region and region information of the cell nucleus from the cell image;

a judging unit to judge whether or not to correct the candidate region of the cell nucleus on the basis of the region information of the cell nucleus; and a correcting unit to correct the candidate region of the cell nucleus on the basis of a judgement result by the judging unit and to detect the cell nucleus.

According to another aspect of the present invention, there is provided an image processing program for controlling a computer for detecting a cell nucleus in a cell image in which the cell nucleus is stained to function as:

a region-extracting unit to extract a candidate region and region information of the cell nucleus from the cell image;

a judging unit to judge whether or not to correct the candidate region of the cell nucleus on the basis of the region information of the cell nucleus; and a correcting unit to correct the candidate region of the cell nucleus on the basis of a judgment result by the judging unit and to detect the cell nucleus.

Effects of the Invention

According to the present invention, it is possible to detect an individual cell nucleus without incorrect detection, although the cell nucleus is not stained uniformly or is contiguous with neighboring cell nuclei.

BRIEF DESCRIPTION OF DRAWINGS

FIG. 3 is a flowchart schematically showing a flow of image processing;

FIG. 5 shows examples of binary images, images showing edge intensity, images showing edge angle, and images showing normal line direction of an edge, respectively obtained from a cell image of a clearly-stained cell nucleus, a cell image of a single sparsely-stained cell nucleus, and a cell image of a plurality of stained cells contiguous with each other.

FIG. 10 is a flowchart schematically showing a flow of judging/correcting processing.

FIG. 20A is an example of a cell image of a clearly-stained cell nucleus.

FIG. 20B is an example of a cell image of a single sparsely-stained cell nucleus.

FIG. 20C is an example of a cell image of a plurality of stained cells contiguous with each other.

EMBODIMENT FOR CARRYING OUT THE INVENTION

Hereinafter, preferred embodiments of the present invention are described with reference to the drawings.

<Configuration of Pathological Diagnosis Assistance System 10>

Figure 1:
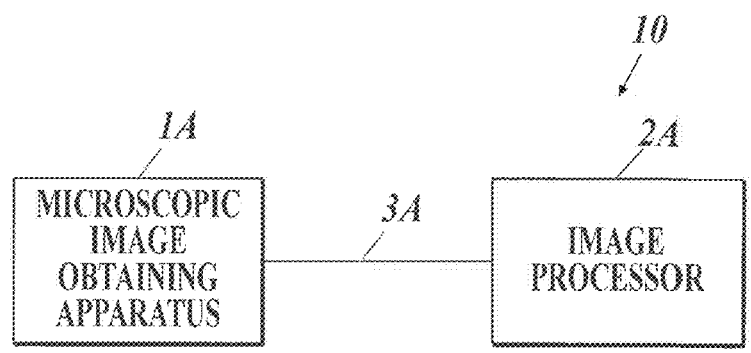
FIG. 1 is a diagram schematically showing a configuration of a pathological diagnosis assistance system.

FIG. 1 shows an example of an entire configuration of a pathological diagnosis assistance system 10.

The pathological diagnostic assistance system 10 obtains a microscopic image of a tissue slice of a human body stained with a predetermined staining reagent and detects a cell nucleus in the tissue slice of the observation target by analyzing the obtained microscopic image.

As shown in FIG. 1, the pathological diagnosis assistance system 10 includes a microscopic image obtaining apparatus 1A and an image processing device 2A connected to each other through an interface such as a cable 3A so as to be able to transmit and receive data.

The connecting system of the microscopic image obtaining apparatus 1A and the image processing device 2A is not particularly limited. For example, the microscopic image obtaining apparatus 1A and the image processing device 2A can be connected by a LAN (Local Area Network) or can be connected wirelessly.

The microscopic image obtaining apparatus 1A is a publically-known optical microscope with a camera. The microscopic image obtaining apparatus 1A obtains the microscopic image of the tissue slice placed on the slide on a slide fixing stage, and transmits the image to the image processing device 2A.

The microscopic image obtaining apparatus 1A includes an irradiating unit, an image forming unit, an imaging unit, a communication I/F, etc. The irradiating unit includes a light source, filter, etc., and irradiates the tissue slice placed on the slide on the slide fixing stage with light. The image forming unit includes an ocular lens, an object lens, etc., and forms an image of transmitted light or reflected light from the tissue slice on the slide due to the irradiated light. The imaging unit is a camera provided in a microscope which includes a CCD (Charge Coupled Device) sensor, etc., and images an image formed on an image forming face by the image forming unit to generate digital image data of the microscopic image. The communication I/F transmits the generated image data of the microscopic image to the image processing device 2A.

The microscopic image obtaining apparatus 1A includes a bright field unit combining the irradiating unit and the image forming unit suitable for bright field observation.

The microscopic image obtaining apparatus 1A is not limited to a microscope with a camera. For example, a virtual microscope slide creating apparatus which scans a slide on a slide fixing stage of a microscope and obtains a microscopic image of the entire tissue slice can be used (for example, see Japanese Patent Application Laid-Open Publication No. 2002-514319). According to the virtual microscope slide creating apparatus, image data with which the entire image of the tissue slice on the slide can be viewed at once on the display section can be obtained.

The image processing device 2A analyzes the microscopic image transmitted from the microscopic image obtaining apparatus 1A and detects the cell nucleus in the tissue slice of the observation target.

Figure 2:
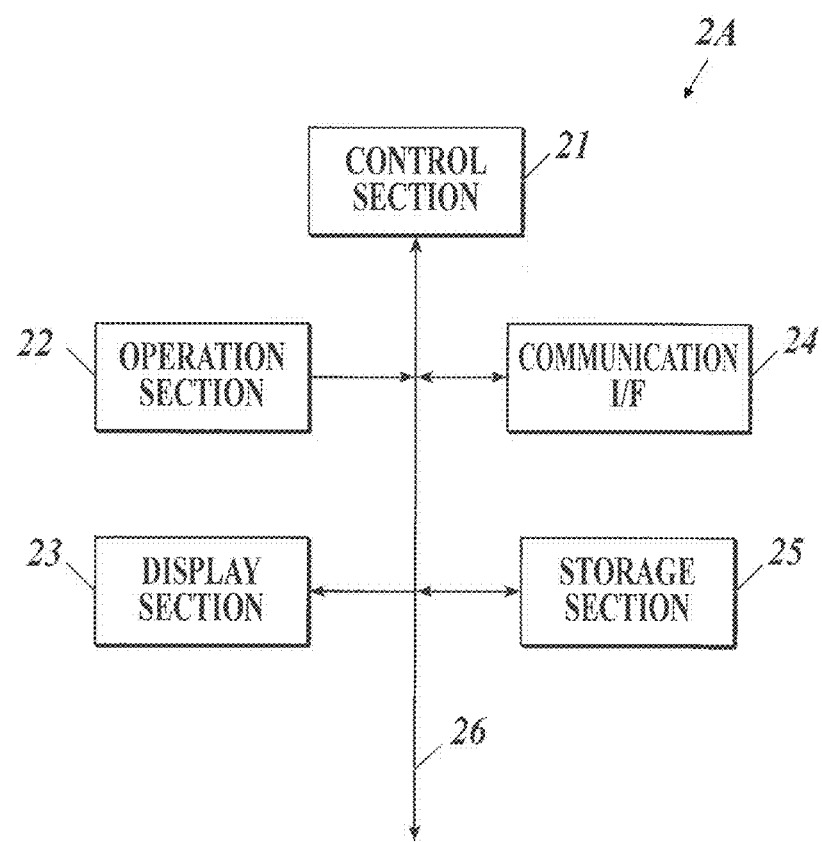
FIG. 2 is a block diagram schematically showing a functional configuration of an image processing device.

FIG. 2 shows an example of a functional configuration of the image processing device 2A.

As shown in FIG. 2, the image processing device 2A includes a control section 21, an operation section 22, a display section 23, a communication I/F 24, a storage section 25, and the like, and each section is connected through a bus 26.

The control section 21 includes a CPU (Central Processing Unit), a RAM (Random Access Memory), and the like, performs various processing in coordination with various programs stored in the storage section 25, and collectively controls the operation of the image processing device 2A.

For example, the control section 21 performs image processing (see FIG. 3) in coordination with an image processing program stored in the storage section 25, and realizes functions as a region-extracting unit, a judging unit, a correcting unit, and an edge-extracting unit.

The operating section 22 includes a keyboard provided with character input keys, numeric input keys, and various function keys and a pointing device such as a mouse, and outputs depression signals of the pressed keys of the keyboard and operation signals of the mouse as the input signal to the control section 21.

The display section 23 includes a monitor such as a CRT (Cathode Ray Tube), an LCD (Liquid Crystal Display), etc., and displays various screens according to an instruction of a display signal input from the control section 21.

The communication I/F 24 is an interface for transmitting and receiving data with external devices such as the microscopic image obtaining apparatus 1A. The communication I/F 24 functions as the input unit of a cell image.

The storage section 25 includes, for example, an HDD (Hard Disk Drive), a nonvolatile semiconductor memory, etc. The storage section 25 stores various programs and various pieces of data as described above.

Other than the above, the image processing device 2A can include a LAN adaptor, a router, etc., and can be connected to external devices through a communication network such as a LAN.

The image processing device 2A of the present embodiment analyzes the microscopic image (a cell image) transmitted from the microscopic image obtaining apparatus 1A.

A "cell image" is a microscopic image obtained by forming an enlarged image of a tissue slice stained with a reagent capable of staining cell nucleus, such as a reagent for hematoxylin stain (H staining reagent) or a reagent for hematoxylin-eosin stain (HE staining reagent) in a bright field in the microscopic image obtaining apparatus 1A, and capturing the image. The bright field image is a cell shape image showing shapes of cells in the tissue slice. Hematoxylin (H) is a blue purple dye and stains the cell nucleus, bone tissue, a portion of cartilage tissue, serous fluid component etc. (basophilic tissue, etc.). Eosin (E) is a red to pink dye and stains cytoplasm, connective tissue of soft tissue, red blood cell, fibrin, endocrine granule, etc. (eosinophilic tissue, etc.).

<Operation of Pathological Diagnosis Assistance System 10 (Including the Method of Image Processing)>

Below, the operation of obtaining the above described cell image and performing analysis in the pathological diagnosis assistance system 10 is described.

First, the operator stains the tissue slice using an H staining reagent or a HE staining reagent.

Subsequently, the cell image is obtained with the microscopic image obtaining apparatus 1A by steps (a1) to (a3).

(a1) The operator mounts the tissue slice in which a cell nucleus is stained using an H staining reagent or a HE staining reagent on a slide, and places the slide on a slide fixing stage of the microscopic image obtaining apparatus 1A.

(a2) The bright field unit is set, the capturing magnification and focus are adjusted, and the region of the observation target of the tissue slice is positioned in the visual field.

(a3) Capturing is performed with the capturing unit to generate the image data of the cell image, and the image data is transmitted to the image processing device 2A.

Subsequently, image processing is performed on the basis of the cell image by the image processing device 2A.

FIG. 3 is a flowchart describing the image processing in the image processing device 2A.

The image processing shown in FIG. 3 is performed by the control section 21 in coordination with the image processing program stored in the storage section 25. The control section 21 performs the processing as described below in accordance with the image processing program.

First, when the cell image is input from the microscopic image obtaining apparatus 1A through the communication I/F 24 (step S10), color information is obtained from the cell image, binary image is generated by performing a threshold processing of the cell image on the basis of a specific color component extracted from the color information, and a candidate region and region information of a cell nucleus are extracted (step S20).

"A candidate region" of a cell nucleus is a region which is a candidate of a cell nucleus among the stained regions in detecting an individual cell nucleus and is considered to be a region deriving from a cell nucleus.

"Region information" of a cell nucleus is information regarding the candidate region of a cell nucleus such as area, shape, etc. Region information includes the presence/absence of structures other than the cell nucleus (such as a nucleolus).

Meanwhile, separately from step S20, when the cell image is input from the microscopic image obtaining apparatus 1A through the communication I/F 24 (step S10), color information is obtained from the cell image and edge information of a cell nucleus is also extracted (step S30).

Figure 4A:
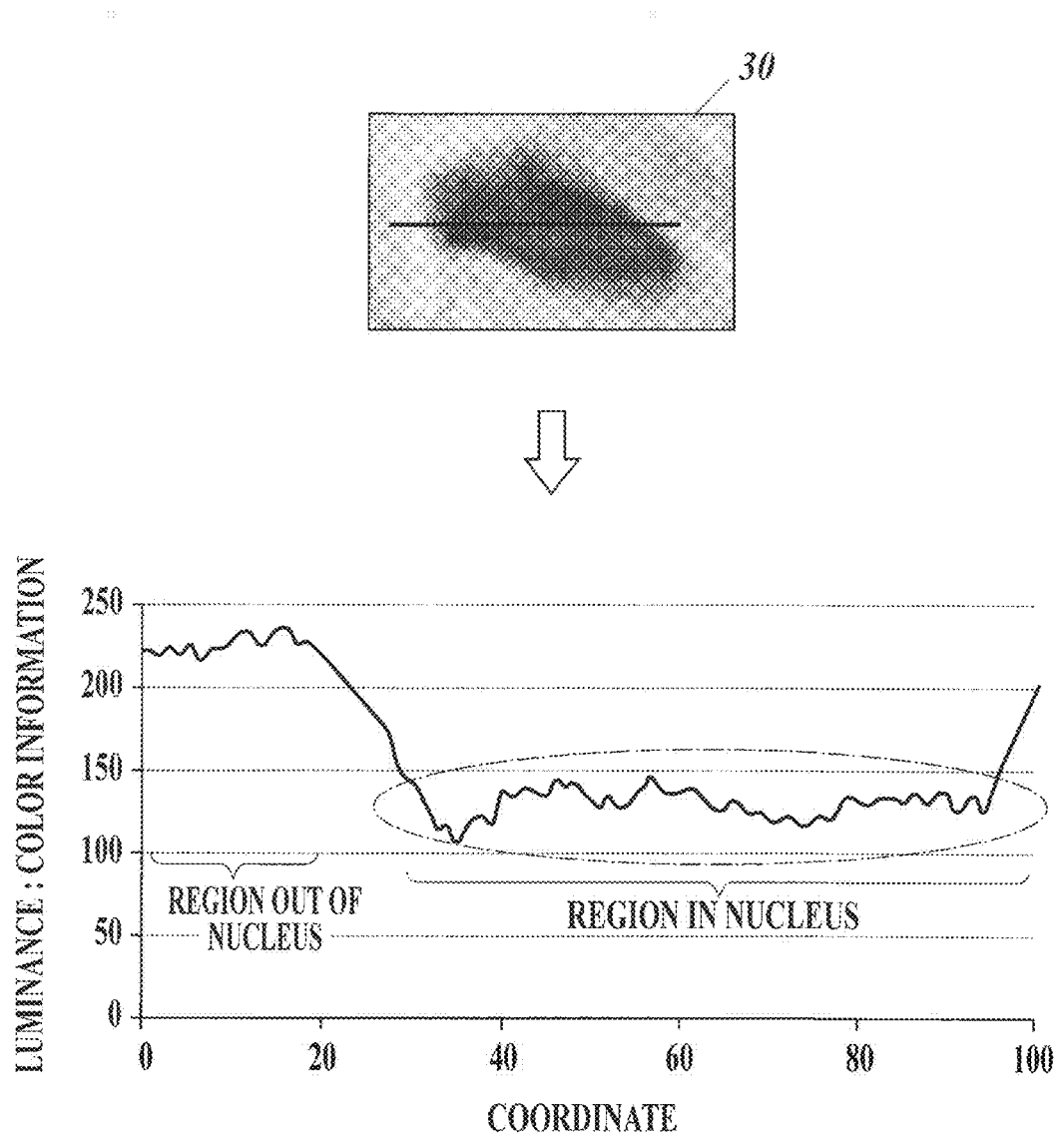
FIG. 4A is a diagram schematically explaining the luminance corresponding to a cell image of a clearly-stained cell nucleus.

For example, as shown in FIG. 4A, according to the luminance calculated from color information obtained from cell image 30 in which a clearly-stained cell nucleus is observed (upper part of the figure), the luminances at the coordinate sites along the straight line in cell image 30 are largely different between in the extranuclear region and in the intranuclear region (lower part of the figure).

Figure 4B:
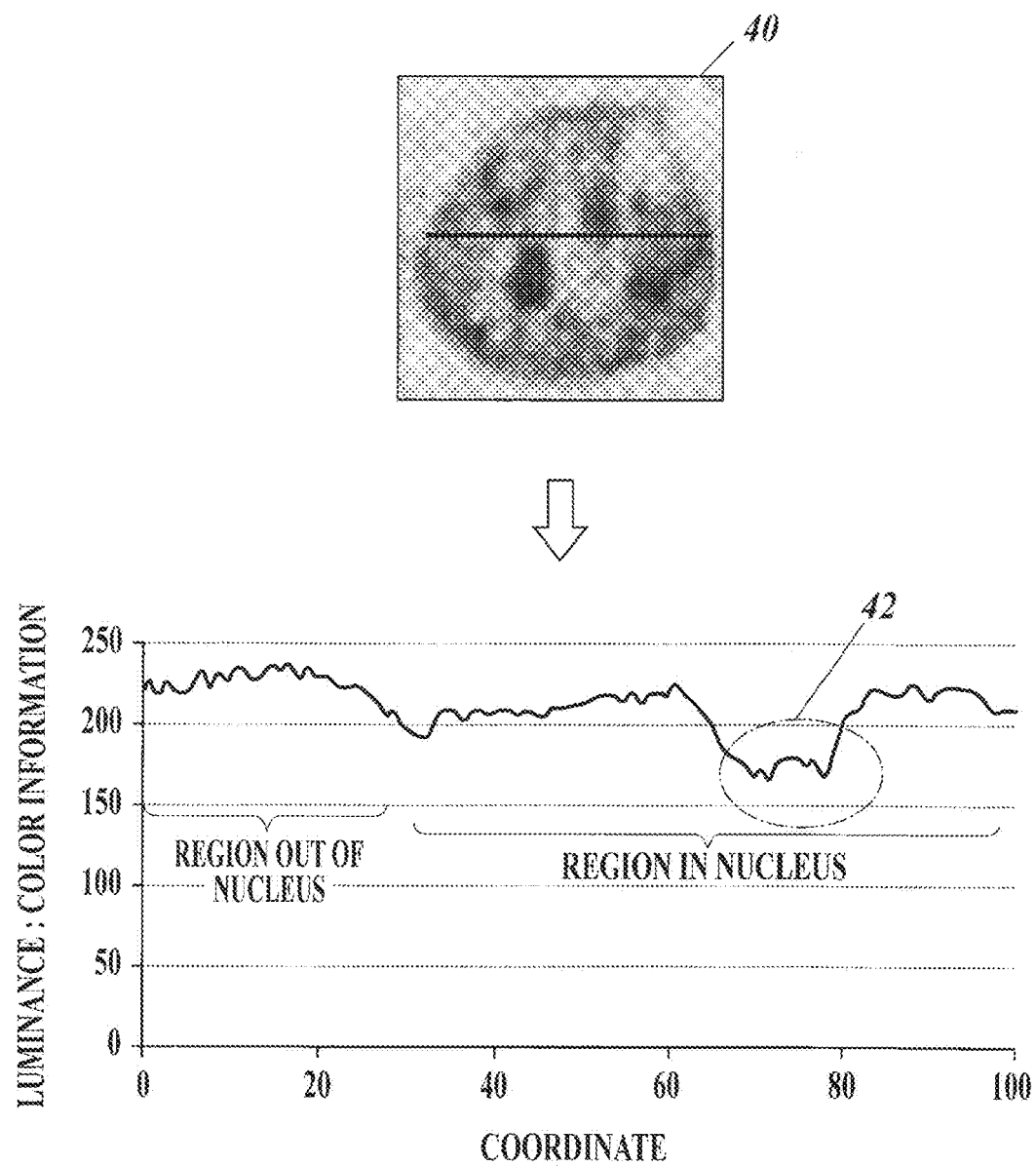
FIG. 4B is a diagram schematically explaining the luminance corresponding to a cell image of a single sparsely-stained cell nucleus.

Meanwhile, as shown in FIG. 4B, according to cell image 40 in which a single sparsely-stained cell nucleus is observed (upper part of the figure), the luminances at the coordinate sites along the straight line in cell image 40 are slightly different between in the intranuclear region and in the extranuclear region. On the basis of a binary image obtained in step S20, only region 42 within the intranuclear region is detected as a candidate region of a cell nucleus (lower part of the figure).

Figure 4C:
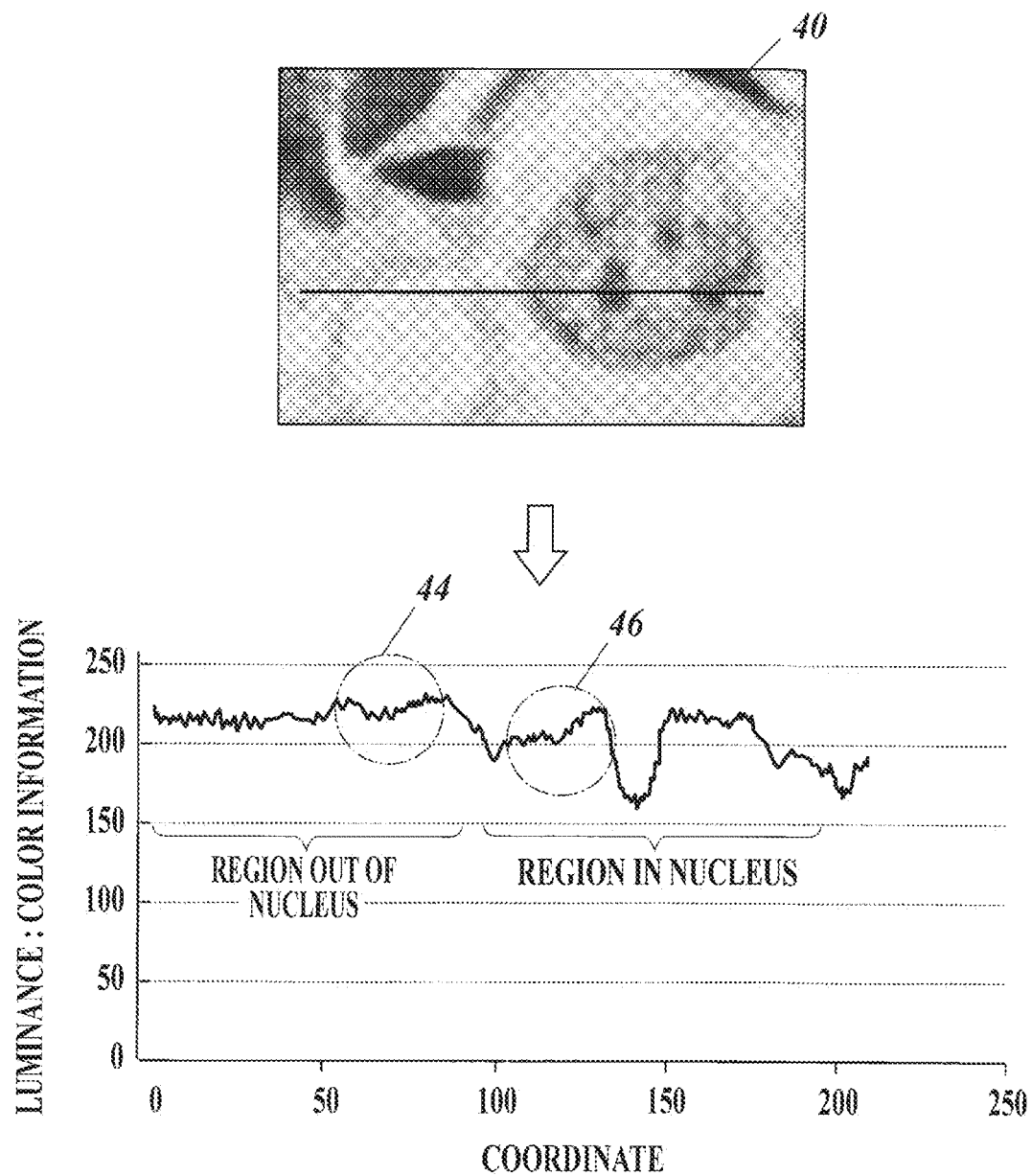
FIG. 4C is a diagram having a wider coordinate range than the diagram in FIG. 4B.

However, as shown in FIG. 4C, even according to cell image 40 (upper part of the figure), the luminances at the coordinate sites of wider range along the straight line in cell image 40 are different between in region 44 in the extranuclear region and in region 46 in the intranuclear region. A boundary line of the cell nucleus can be detected by using edge information (lower part of the figure).

In the present embodiment, as shown in FIG. 5, a candidate region and region information of cell nucleus are extracted from the binary image generated in step S20, and edge information of a cell nucleus is further extracted in step S3 from cell image 30, cell image 40, and cell image 50 in which a plurality of cell nuclei are stained contiguously.

Edge information of a cell nucleus includes edge intensity, edge angle, normal line direction of an edge, and curvature at an edge.

"Edge intensity" is a variation in luminance at the edge of a cell nucleus in a cell image and calculated using a certain filter.

Figure 6A:
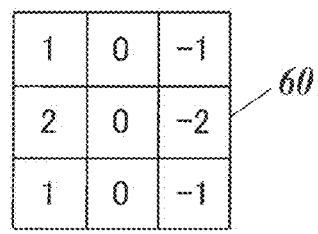
FIG. 6A is an example of a filter used for extracting edge intensity.
Figure 6B:
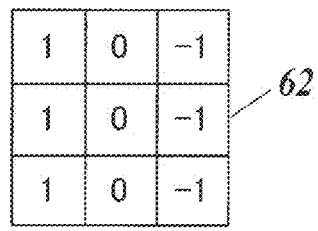
FIG. 6B is an example of a filter used for extracting edge intensity.

As shown in FIG. 6A to FIG. 6B, examples of the certain filter include a sobel filter 60, a differential filter along a primary direction 62, etc. Such filter is also used in extracting edge angle or normal line direction of an edge.

Figure 6C:
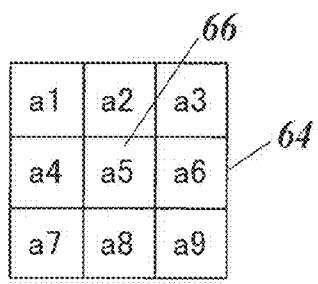
FIG. 6C is a diagram schematically explaining a method of extracting edge intensity.

For example, edge intensity can be extracted by the following operations using a sobel filter 60 for each pixel at the edge. As shown in FIG. 6C, pixel region 64 including an edge (a region of 3 by 3 pixels with target pixel 66 at the center) is selected and the luminance a1 to luminance a9 in pixel region 64 are respectively multiplied by the values in the sobel filter 60, for example, 1 by a1, 0 by a2, −1 by a3, 0 by a8, −1 by a9. The total of the multiplied value is calculated as a luminance of the target pixel 66.

The edge intensity images in FIG. 5 are generated by extracting edge intensity from cell images in step S30. Higher edge intensity is expressed more whitely.

Figure 6D:
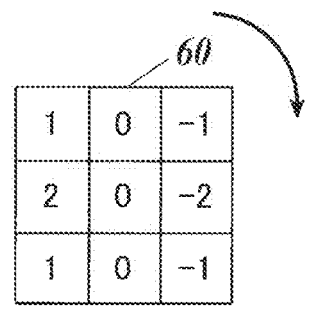
FIG. 6D is a diagram schematically explaining a method of extracting edge angle.

"Edge angle" is angle of tangential line at the edge of a cell nucleus in a cell image. As shown in FIG. 6D, edge intensity at the edge portion is measured with the filter rotating by 5° intervals within the range of 0° to 90°, and the edge angle is determined as the angle of the filter resulting in the maximum edge intensity.

Figure 7A:
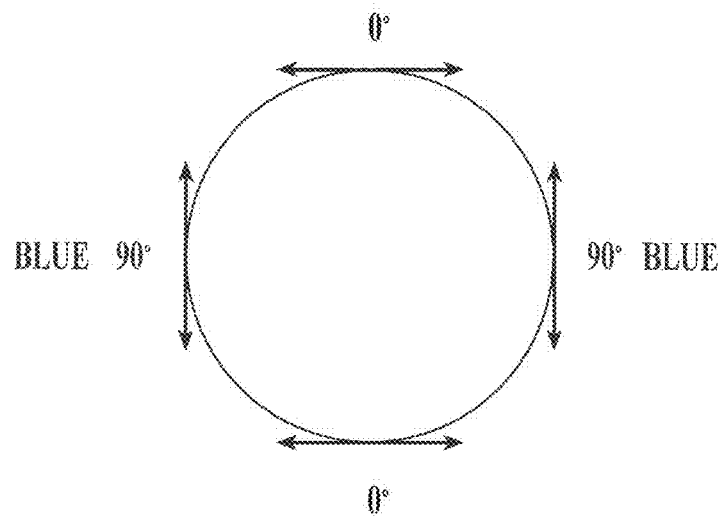
FIG. 7A is a diagram schematically explaining an angle expressed as an edge angle.

In the present embodiment, as shown in FIG. 7A, the angle of a tangential line in horizontal direction is set as 0° and the angle of a tangential line in vertical direction is set as 90° (blue).

The edge angle images in FIG. 5 are generated by extracting edge angle from cell images in step S30. The cell nucleus is expressed by blue shading corresponding to the edge angle.

"A normal line direction of an edge" is a direction corresponding to not only the normal line direction of tangential line at the edge of the cell nucleus in the cell image but also the direction from the extranuclear region to the intranuclear region.

Specifically, edge intensity at the edge portion is measured with the filter rotating by 5° intervals within the range of 0° to 360°, and the normal line direction of an edge is determined as the direction orthogonal to the angle of the filter resulting in the maximum edge intensity and as the direction along which the edge intensity changes from positive to negative.

The concept of positive/negative of the edge intensity is as follows.

Figure 6E:
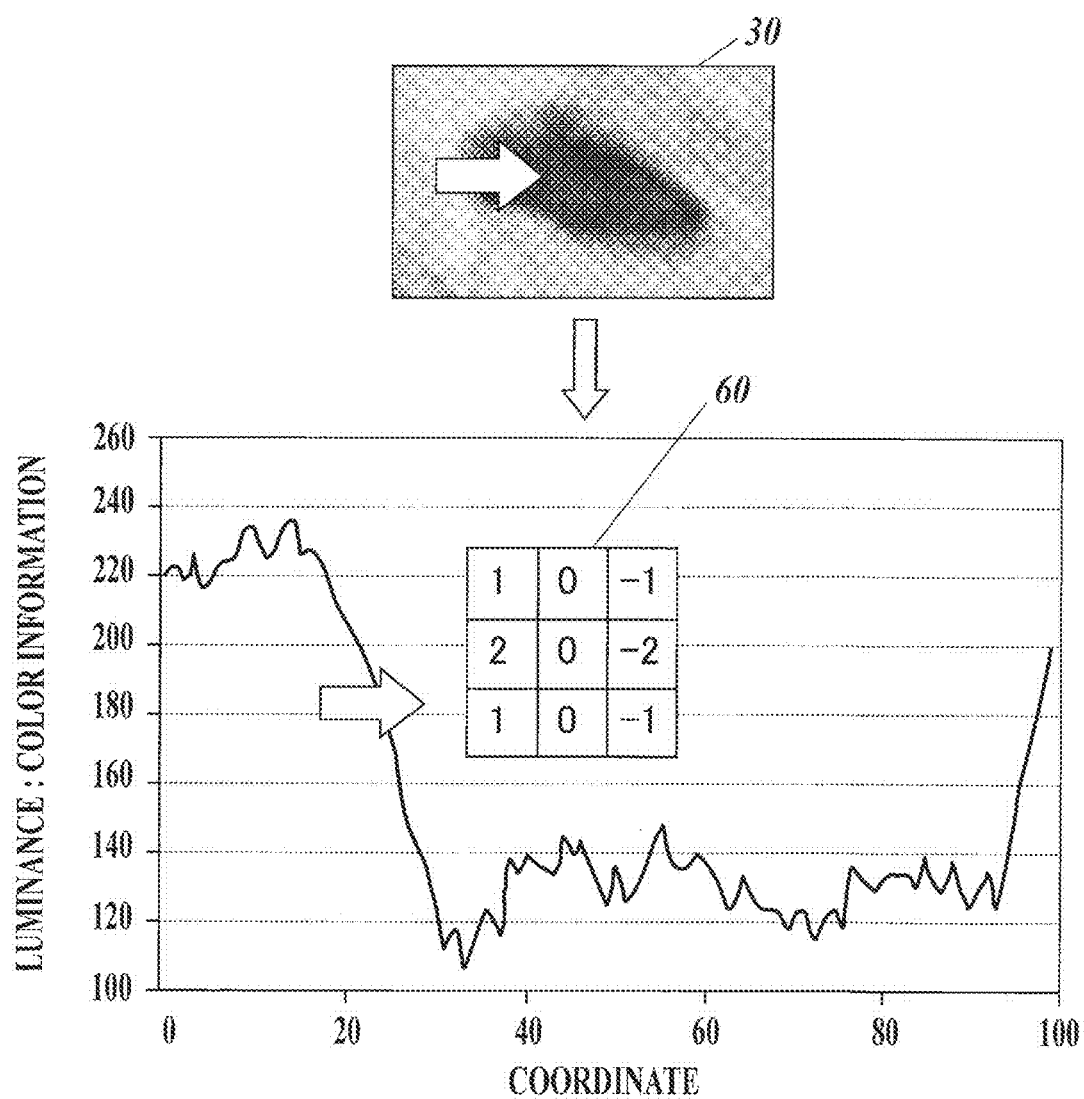
FIG. 6E is a diagram schematically explaining a method of extracting normal line direction of an edge.

For example, as shown by the arrows in FIG. 6E, when edge intensity is determined from the extranuclear region to the intranuclear region using filter 60 in cell image 30, the luminance is high in the extranuclear region and low in the intranuclear region. At the region near the boundary of the extranuclear region and the intranuclear region (boundary region), the high luminance in the extranuclear region is multiplied by the positive value of filter 60 (1, 2, 1) and the low luminance in the intranuclear region is multiplied by the negative value of filter 60 (−1, −2, −1). Accordingly, the luminance of a target pixel is positive in the boundary region near the extranuclear region, due to the large contribution of the high luminance in the extranuclear region. As the site of target pixel changes from the extranuclear region to the intranuclear region, the contribution of the low luminance in the intranuclear region becomes large, and the luminance of a target pixel becomes negative.

Figure 7B:
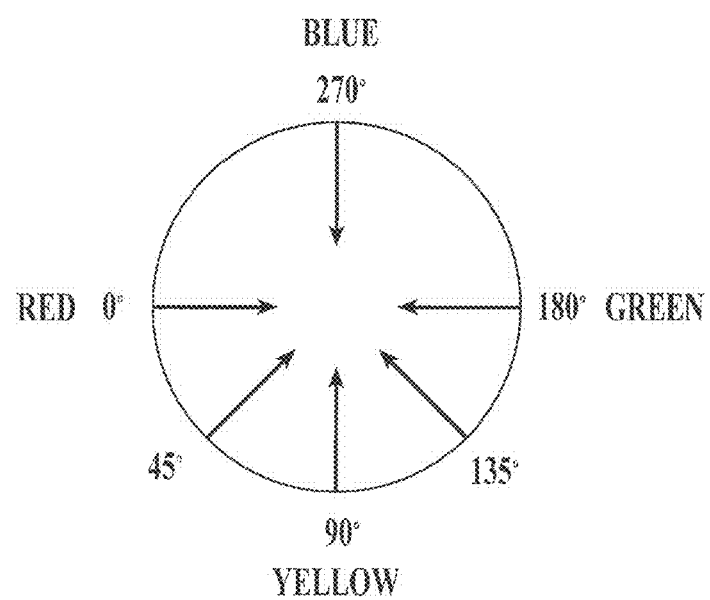
FIG. 7B is a diagram schematically explaining a direction expressed as a normal line direction of an edge.

In the present embodiment, as shown in FIG. 7B, the normal line direction of an edge is determined to be 0° (red), when the normal line direction of tangential line is horizontal and the normal line direction from the extranuclear region to the intranuclear region of the cell nucleus in the cell image is rightward. The normal line direction of an edge is determined to be 90° (yellow), when the normal line direction of tangential line is vertical and the normal line direction from the extranuclear region to the intranuclear region of the cell nucleus in the cell image is upward. The normal line direction of an edge is determined to be 180° (green), when the normal line direction of tangential line is horizontal and the normal line direction from the extranuclear region to the intranuclear region of the cell nucleus in the cell image is leftward. The normal line direction of an edge is determined to be 270° (blue), when the normal line direction of tangential line is vertical and the normal line direction from the extranuclear region to the intranuclear region of the cell nucleus in the cell image is downward.

The images showing normal line direction of an edge in FIG. 5 are generated by extracting normal line directions of an edge from cell images in step S30. The cell nucleus is expressed in red, yellow, green, or blue according to the normal line direction of an edge.

Figure 8A:
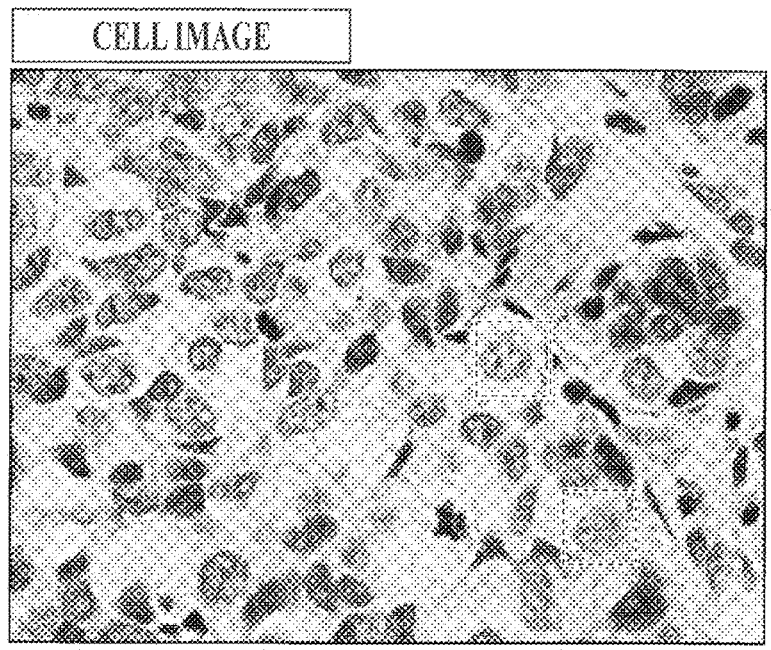
FIG. 8A is an example of a cell image.
Figure 8B:
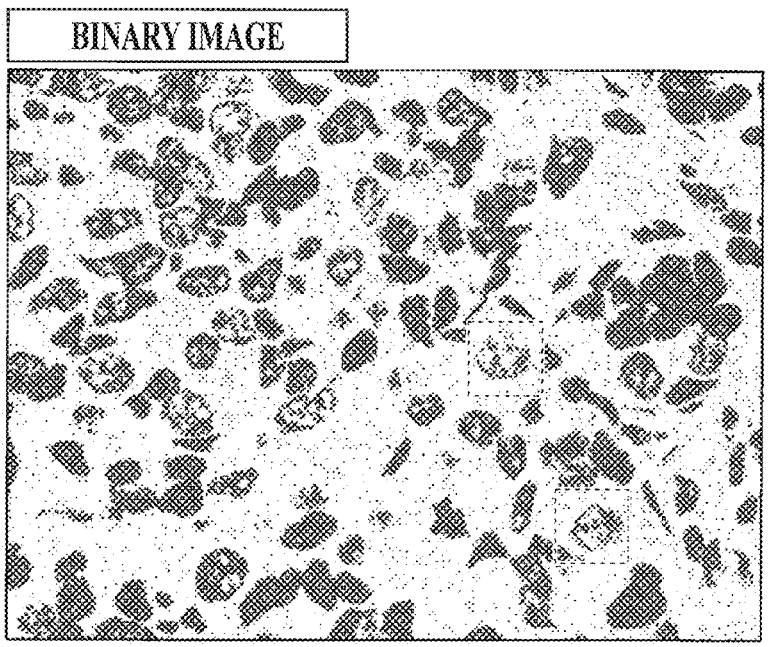
FIG. 8B is an example of a binary image generated from a cell image.
Figure 8C:
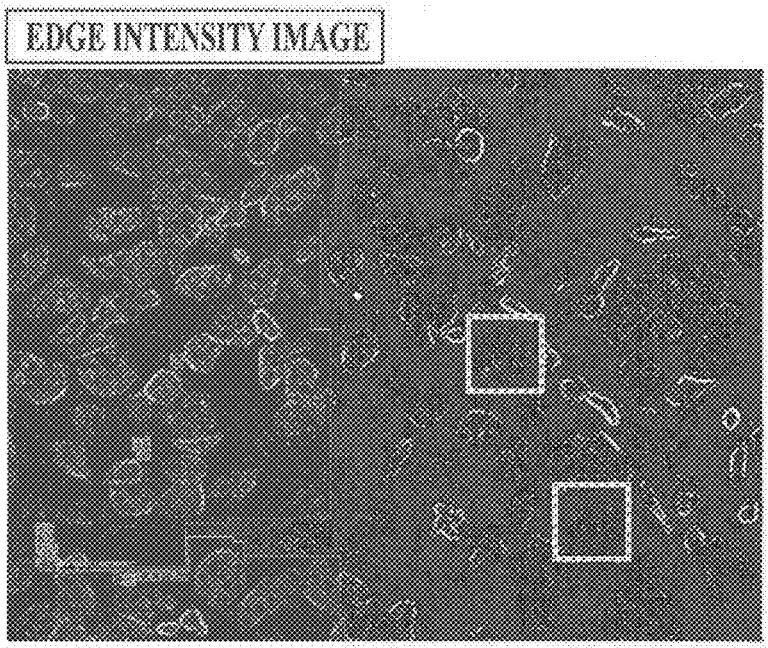
FIG. 8C is an example of an image generated by extracting edge intensities from a cell image.
Figure 8D:
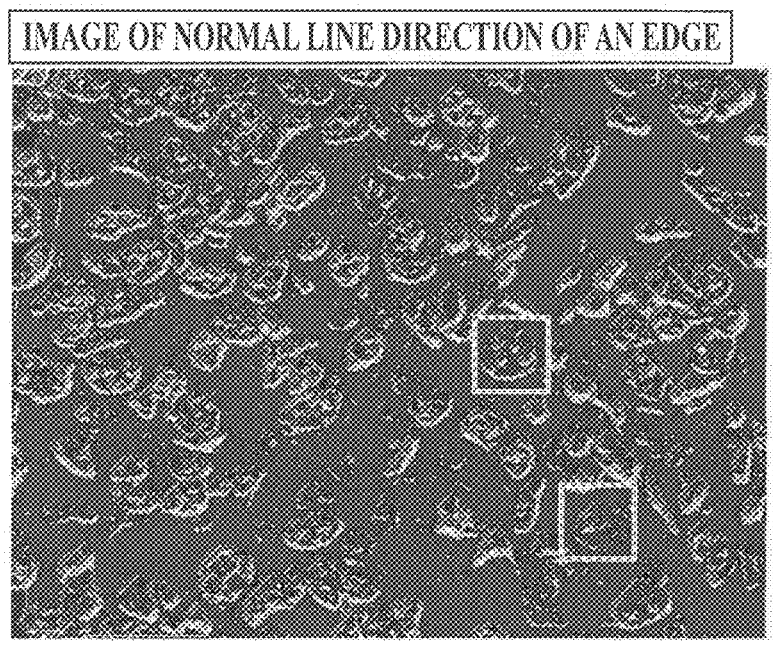
FIG. 8D is an example of an image generated by extracting normal line directions of an edge from a cell image.

FIG. 8A to FIG. 8D each illustrate an example of a cell image (FIG. 8A), a binary image generated from the cell image in step S20 (FIG. 8B), an image generated by extracting edge intensity from the cell image in step S30 (FIG. 8C), and an image generated by extracting normal line directions from the cell image in step S30 (FIG. 8D).

The dotted square frames in each image show the same regions.

"Curvature at the edge" literally means curvature at the edge portion of the cell nucleus in the cell image.

Figure 9A:
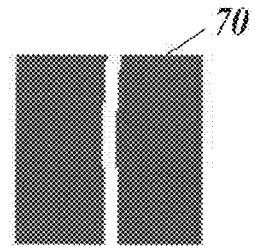
FIG. 9A is an example of a filter used for extracting curvature at an edge.
Figure 9B:
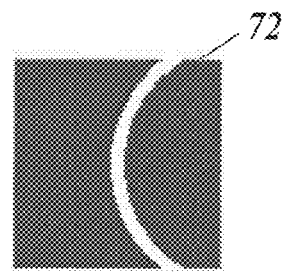
FIG. 9B is an example of a filter used for extracting curvature at an edge.
Figure 9C:
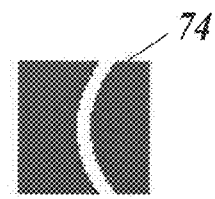
FIG. 9C is an example of a filter used for extracting curvature at an edge.

As shown in FIG. 9A to FIG. 9C, the curvature at the edge can be calculated based on which of the filters 70, 72, or 74 each having a certain curvature matches with an image generated by extracting edge intensity from the cell image.

Figure 9D:
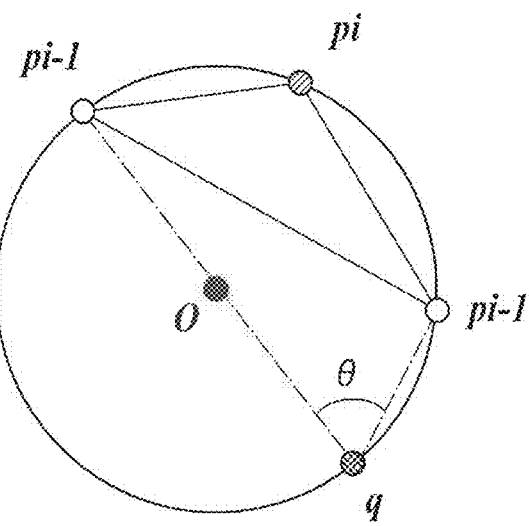
FIG. 9D is a diagram schematically explaining a method of extracting curvature at an edge.

As shown in FIG. 9D, the curvature at the edge may be calculated using a numerical formula based on three points, one point ($P_i$) on the fine line obtained from the edge portion in the cell image and two points ($P_{i-1}$) around the point ($P_i$).

Figure 9E:
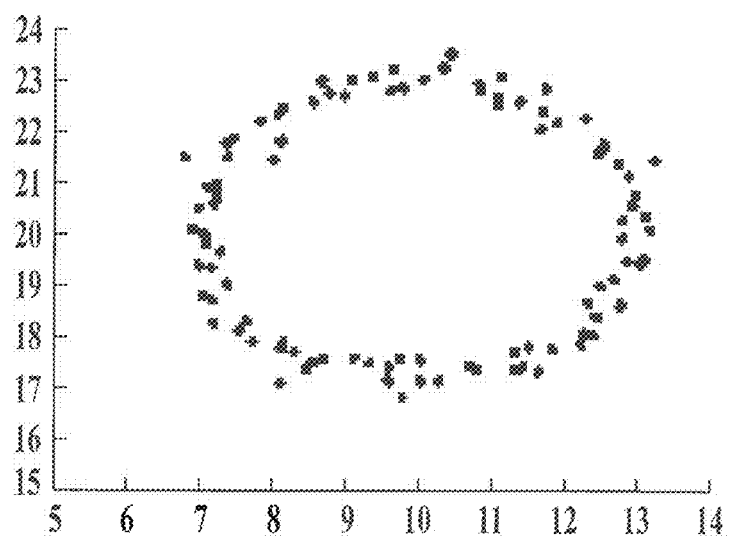
FIG. 9E is a diagram schematically explaining a method of extracting curvature at an edge.

As shown in FIG. 9E, the curvature at the edge may be calculated using the least squares method based on a plurality of points on the fine line obtained from the edge portion in the cell image.

Subsequently, as shown in FIG. 3, whether to correct the candidate region of the cell nucleus extracted in step S20 or not is judged on the basis of the region information of the cell nucleus extracted in step S20 and the edge information of the cell nucleus extracted in step S30 (step S40).

In step S40, at first, whether to correct the candidate region of the cell nucleus or not is judged based on the region information of the cell nucleus as shown in FIG. 10 (step S41).

Figure 11:
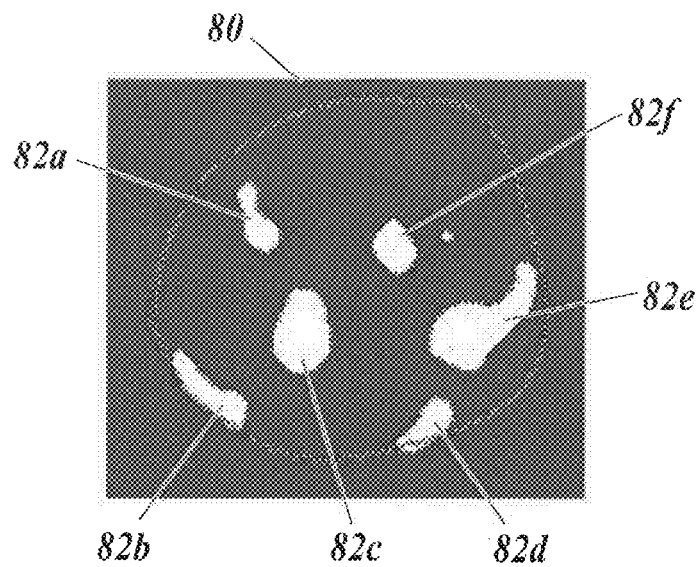
FIG. 11 is a diagram showing a condition in which integration of candidate regions of a cell nucleus is required.

In step S41, as shown in FIG. 11 for example, region 80 within a certain range from the candidate region of the cell nucleus is extracted, and it is judged based on the region information of the cell nucleus whether a plurality of small candidate regions 82a to 82f of cell nucleus are present in region 80 or not. If a plurality of small candidate regions 82a to 82f of cell nucleus are judged to be present in region 80, the area and/or the concentration of candidate regions 82a to 82f of cell nucleus in region 80 are calculated.

Subsequently,
whether the area (total area) of candidate regions 82a to 82f is less than a certain threshold value (a condition 1-1) or not; and/or
whether the concentration of candidate regions 82a to 82f is more than a certain threshold value (a condition 1-2) or not are judged. When the conditions 1-1 and/or 1-2 are satisfied, the candidate region 82 is judged to be in need of integration and the processing moves to step S42.

The processing may move to step S42 either when both of the conditions 1-1 and 1-2 are satisfied or when any one of the conditions 1-1 or 1-2 is satisfied.

In FIG. 11, the gray solid line means the actual cell nucleus.

Figure 12:
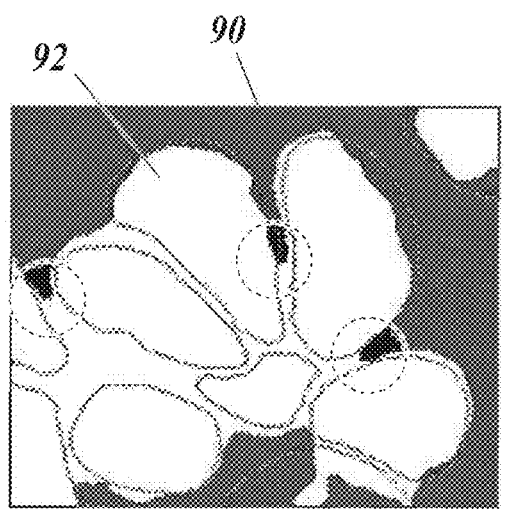
FIG. 12 is a diagram showing a condition in which division of a candidate region of cell nucleus is required.

Meanwhile, as shown in FIG. 12 for example, region 90 within a certain range from the candidate region of the cell nucleus is extracted, and it is judged based on the region information of the cell nucleus whether a single large candidate region 92 of cell nucleus is present in the region 90 or not. If a large candidate region 92 of cell nucleus is judged to be present in region 90, the area and/or the circularity of candidate region 92 of cell nucleus in region 90 are calculated and the presence of a concave point and/or a plurality of nucleoli are detected.

Subsequently,
whether the area of candidate region 92 is more than a certain threshold value (a condition 2-1) or not;
whether the circularity of candidate region 92 is less than a certain threshold value (a condition 2-2) or not;
whether a concave point is present in the candidate region 92 (a condition 2-3, see dotted lines in FIG. 12) or not; and/or
whether a plurality of nucleoli are present in the candidate region 92 (a condition 2-4) or not are judged. When the conditions 2-1 to 2-4 are satisfied, the candidate region 92 is judged to be in need of division and the processing moves to step S46.

The processing may move to step S46 either when all of the conditions 2-1 to 2-4 are satisfied, when any three of the conditions are satisfied, when any two of the conditions are satisfied, or when any one of the conditions is satisfied.

In FIG. 12, the gray solid lines mean the actual cell nuclei.

As shown in FIG. 10, in step S42, whether to actually integrate the plurality of small candidate regions of the cell nucleus or not is judged based on the region information of the cell nucleus and the edge information of the cell nucleus (step S42).

Figure 13A:
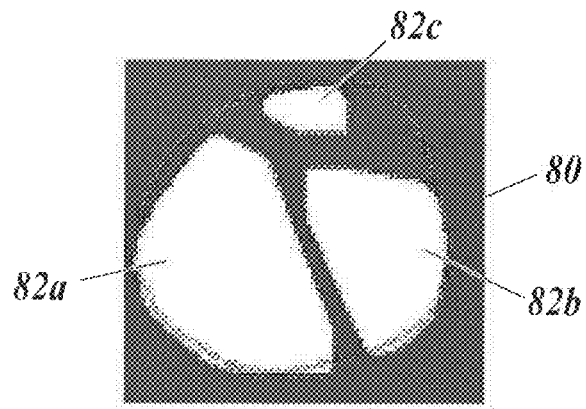
FIG. 13A is a diagram schematically explaining one of the processes, from judging processing to judge whether a candidate region of a cell nucleus needs to be integrated or not to integration processing to integrate the candidate regions of a cell nucleus.

In step S42, as shown in FIG. 13A, the area and/or the circularity of candidate regions 82a to 82f in the region 80 are calculated, based on the region information of the cell nucleus. The continuity of normal line directions of the edge, the total value of angles of normal line directions of an edge, and/or curvature at the edge are calculated or detected from candidate regions 82a to 82f in the region 80, based on the edge information of cell nucleus.

Subsequently,
whether the area (total area) of candidate regions 82a to 82c is less than a certain threshold value (a condition 3-1Q) or not;
whether the circularity of candidate regions 82a to 82c are less than a certain threshold value (a condition 3-2Q) or not;
whether the continuity of normal line directions of the edge is present (a condition 3-3Q) or not;
whether the total value of angles of normal line directions of an edge is distant from 0° (a condition 3-4Q) or not; and/or
whether the curvatures at the edge of candidate regions 82a to 82c are different from each other (a condition 3-5Q) or not are judged. When the conditions 3-1Q to 3-5Q are satisfied, the candidate region 82 is judged to be actually in need of integration and the processing moves to step S43.

The processing may move to step S43 either when all of the conditions 3-1Q to 3-5Q are satisfied, when any four of the conditions are satisfied, when any three of the conditions are satisfied, when any two of the conditions are satisfied, or when any one of the conditions is satisfied.

Regarding the condition 3-1Q, when the area (total area) of candidate regions 82a to 82c is small (less than the certain threshold value), it is considered that only a part of the cell nucleus is detected and therefore candidate regions 82a to 82c are to be integrated.

Regarding the condition 3-2Q, when the circularity of candidate regions 82a to 82c is low (lower than the certain threshold value) in spite of the high circularity of a general cell nucleus, it is considered that only a part of the cell nucleus is detected and therefore candidate regions 82a to 82c are to be integrated.

Figure 14A:
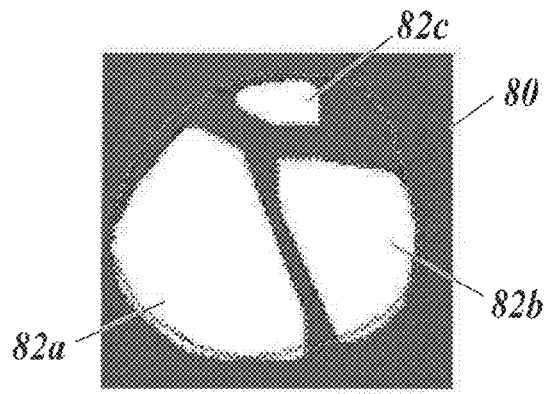
FIG. 14A is a diagram schematically explaining a presence/absence of continuity of normal line directions of an edge.
Figure 14B:
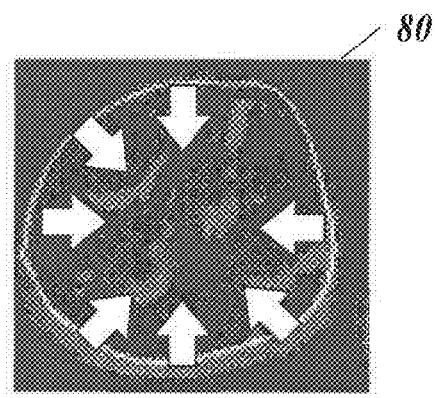
FIG. 14B is a diagram schematically explaining a presence/absence of continuity of normal line directions of an edge.
Figure 14C:
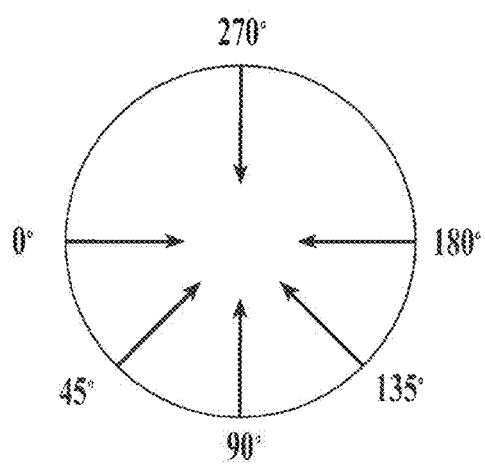
FIG. 14C is a diagram schematically explaining a presence/absence of continuity of normal line directions of an edge.

Regarding the condition 3-3Q, as shown in FIGS. 14A to 14C, the outlines of candidate regions 82a to 82c are connected and the presence of continuity of the normal line directions obtained from the connected outlines is judged, for example, the directions in the order of 0°, 90°, 180°, 270°, and 0°. If continuity is judged to be present, it is considered that the candidate regions 82a to 82c surrounded by the outline are to be integrated.

Regarding the condition 3-4Q, the outlines of candidate regions 82a to 82c are connected and the rotation angle of the filter is changed from the range of 0° to 360° to the range of −180° to 0°, further to 180°. It is judged whether the total value of angles of normal line directions of an edge goes away from 0° by the change of the rotation angle of the filter. When the total value of angles of normal line directions of an edge goes away from 0°, it is considered that only a part of the cell nucleus is detected and therefore candidate regions 82a to 82c are to be integrated.

Regarding the condition 3-5Q, when the curvatures at the edge of candidate regions 82a to 82c are different from each other, it is considered that only a part of the cell nucleus is detected and therefore candidate regions 82a to 82c are to be integrated.

Figure 13B:
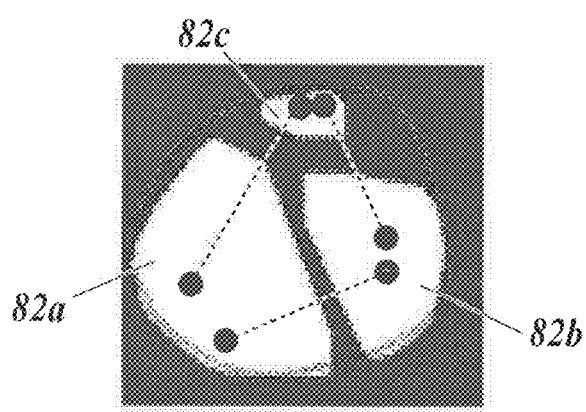
FIG. 13B is a diagram schematically explaining one of the processes, from judging processing to judge whether a candidate region of a cell nucleus needs to be integrated or not to integration processing to integrate the candidate regions of a cell nucleus.

In step S43, as shown in FIG. 13B, the candidate regions 82b and 82c which are close to (within a certain distance from) the candidate region 82a are searched and grouped. The candidate regions 82a and 82c and the candidate regions 82a and 82b, which are respectively close to the candidate regions 82b and 82c, are searched and grouped as well.

Figure 13C:
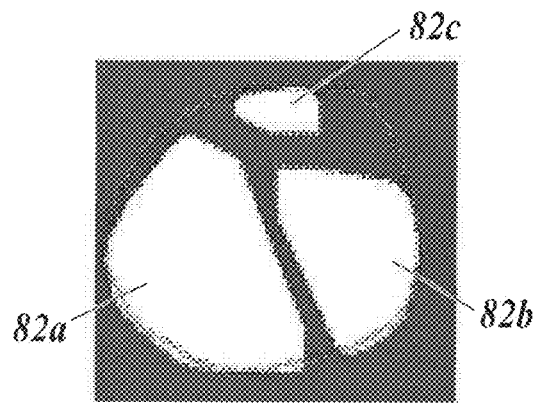
FIG. 13C is a diagram schematically explaining one of the processes, from judging processing to judge whether a candidate region of a cell nucleus needs to be integrated or not to integration processing to integrate candidate regions of a cell nucleus.

Subsequently, as shown in FIG. 13C, the grouped candidate regions 82a to 82c are determined whether to satisfy the following conditions similar to the conditions 3-1Q to 3-5Q (step S44);

whether the area (total area) of candidate regions 82a to 82c is equal to or more than a certain threshold value (a condition 3-1A) or not;
whether the circularity of candidate regions 82a to 82c are equal to or more than a certain threshold value (a condition 3-2A) or not;
whether continuity of normal line directions of the edge is present (a condition 3-3A) or not;
whether the total value of angles of normal line directions of an edge is within a certain range from 0° (a condition 3-4A) or not; and/or
whether the difference between the curvatures at the edge of candidate regions 82a to 82c becomes smaller and is within a certain range (a condition 3-5A) or not.

When the conditions 3-1A to 3-5A are satisfied, integration processing of the candidate regions 82a to 82c is performed (step S45).

The processing may move from step S44 to step S45 either when all of the conditions 3-1A to 3-5A are satisfied, when any four of the conditions are satisfied, when any three of the conditions are satisfied, when any two of the conditions are satisfied, or when any one of the conditions is satisfied.

Figure 13D:
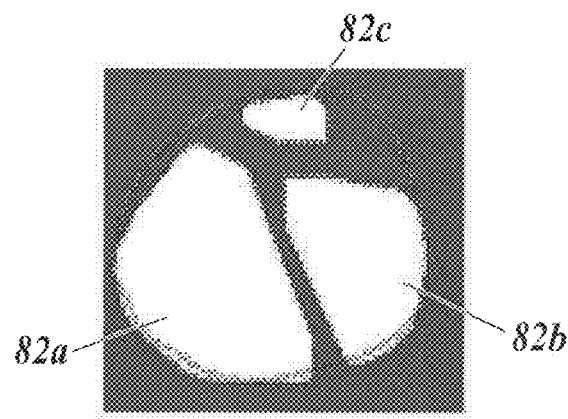
FIG. 13D is a diagram schematically explaining one of the processes, from judging processing to judge whether a candidate region of a cell nucleus needs to be integrated or not to integration processing to integrate candidate regions of a cell nucleus.
Figure 13E:
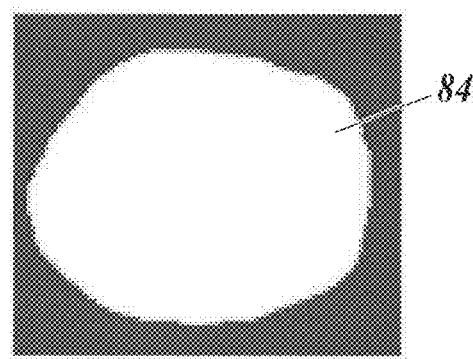
FIG. 13E is a diagram schematically explaining one of the processes, from judging processing to judge whether a candidate region of a cell nucleus needs to be integrated or not to integration processing to integrate candidate regions of a cell nucleus.

In step S45, as shown in FIGS. 13D to 13E, the grouped candidate regions 82a to 82c are integrated to a single region 84.

Figure 15A:
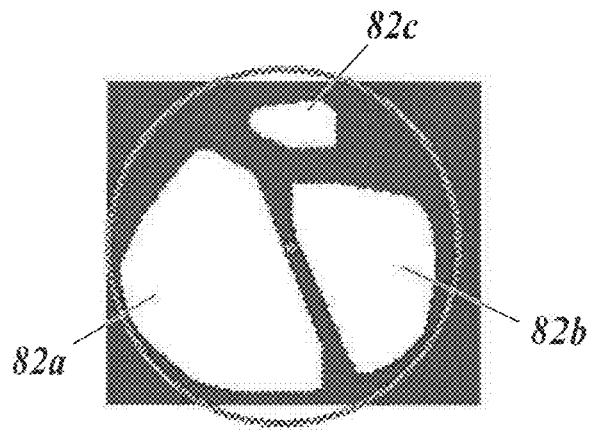
FIG. 15A is an example of integration processing of candidate regions of a cell nucleus.

Specifically, as shown in FIG. 15A, the centroid is calculated from candidate regions 82a to 82c, a circle including candidate regions 82a to 82c are made from the centroid, and candidate regions 82a to 82c are integrated within the circle.

Figure 15B:
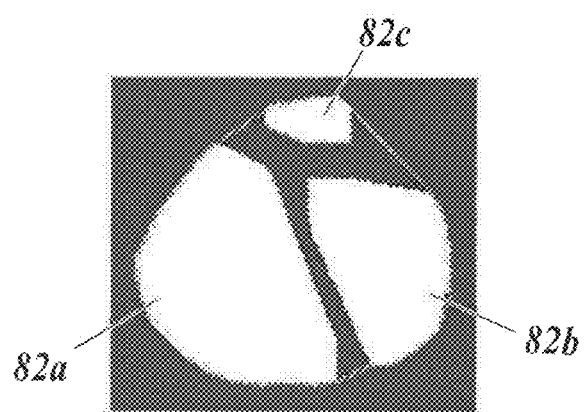
FIG. 15B is an example of integration processing of candidate regions of a cell nucleus.

As shown in FIG. 15B, candidate regions 82a to 82c may be integrated within the region surrounded by the outlines of candidate regions 82a to 82c and straight lines connecting the outlines of candidate regions 82a to 82c.

Figure 15C:
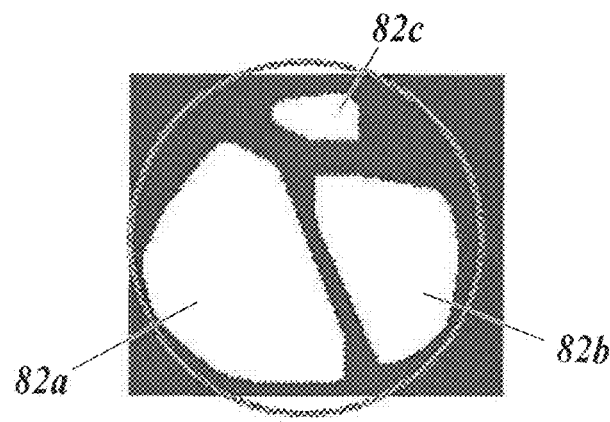
FIG. 15C is an example of integration processing of candidate regions of a cell nucleus.

As shown in FIG. 15C, candidate regions 82a to 82c may be integrated within a circle having the center point and a radius calculated using the least squares method.

Figure 16A:
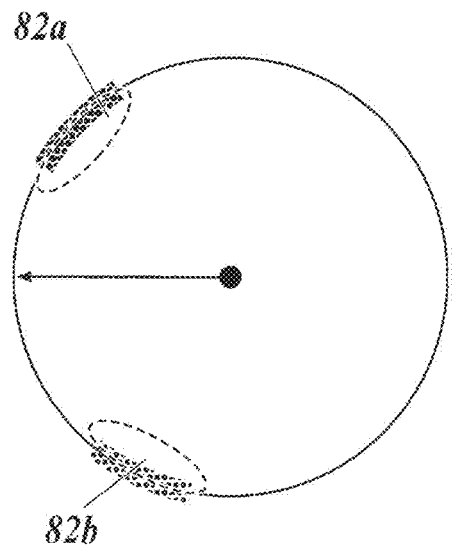
FIG. 16A is an example of integration processing of candidate regions of a cell nucleus.

As shown in FIG. 16A, candidate regions 82a to 82b may be integrated within a circle having the center point and a radius calculated on the basis of curvatures at the edge of the outlines of candidate regions 82a to 82b.

Figure 16B:
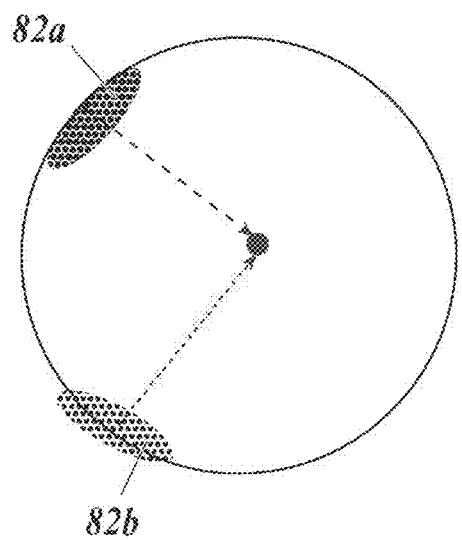
FIG. 16B is an example of integration processing of candidate regions of a cell nucleus.

As shown in FIG. 16B, candidate regions 82a to 82b may be integrated within a circle including candidate regions 82a and 82b from the intersection based on the normal line directions of edge obtained from the outlines of candidate regions 82a to 82b.

Figure 16C:
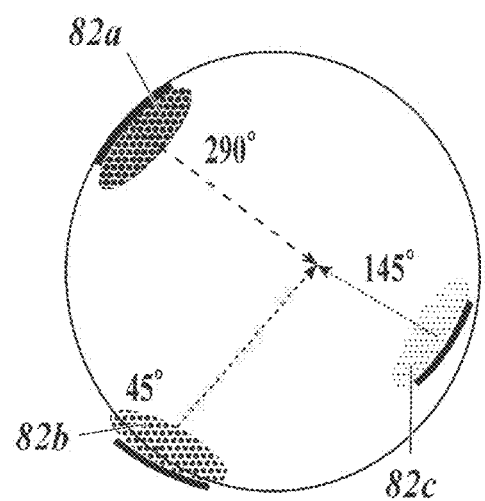
FIG. 16C is an example of integration processing of candidate regions of a cell nucleus.

As shown in FIG. 16C, candidate regions 82a to 82c may be integrated within a circle including candidate regions 82a to 82c from the intersection based on the normal line directions of edge, which are in the order of 45°, 145°, and 290°, obtained from the outlines of candidate regions 82a to 82c.

Figure 16D:
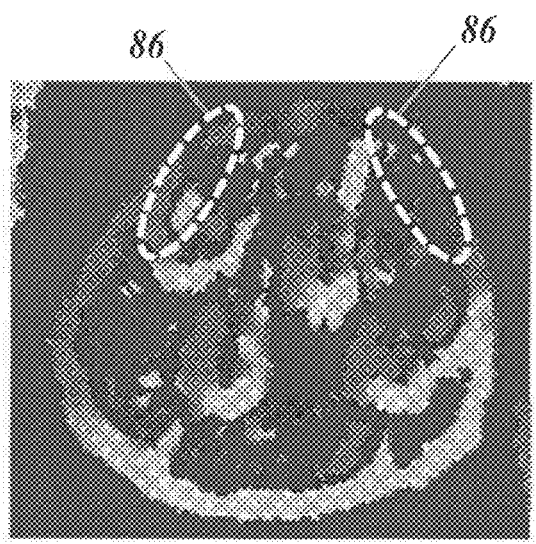
FIG. 16D is an example of integration processing of candidate regions of a cell nucleus.

As shown in FIG. 16D, when the outline of candidate region is almost closed but has missing parts in the image generated by extracting normal line directions of edge from the cell image, the candidate regions may be integrated within the region surrounded by the outlines of candidate regions and linear or curved lines which connect the outlines across the missing parts 86.

Meanwhile, as shown in FIG. 10, in step S46, whether to actually divide the single large candidate region of the cell nucleus or not is judged based on the region information of the cell nucleus and the edge information of the cell nucleus (step S46).

Figure 17A:
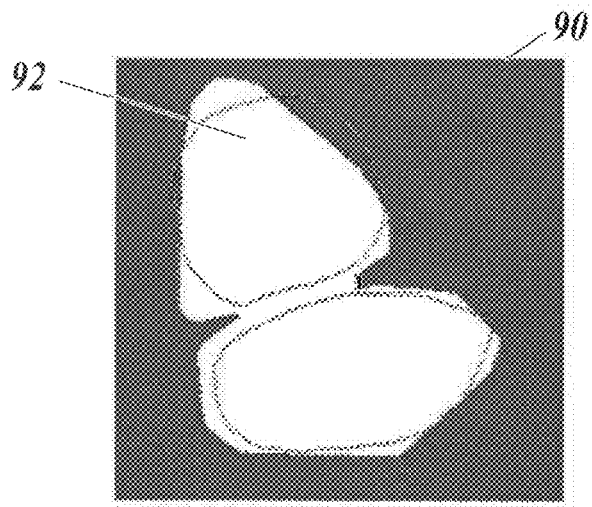
FIG. 17A is a diagram schematically explaining one of the processes, from judging processing to judge whether a candidate region of a cell nucleus needs to be divided or not to division processing to divide the candidate region of cell nucleus.

In step S46, as shown in FIG. 17A, the area and/or the circularity of candidate region 92 in the region 90 are calculated, and the presence of a concave point and/or a plurality of nucleoli are detected in candidate region 92 in the region 90 based on the region information of the cell nucleus. The continuity of normal line directions of the edge, the total value of angles of normal line directions of an edge, and/or curvature at the edge are calculated or detected from candidate region 92 in the region 90 based on the edge information of cell nucleus.

Subsequently,
whether the area of candidate region 92 is more than a certain threshold value (a condition 4-1Q) or not;
whether the circularity of candidate region 92 is less than a certain threshold value (a condition 4-2Q) or not;
whether a concave point is present in the candidate region (a condition 4-3Q) or not;
whether a plurality of nucleoli are present in the candidate region 92 (a condition 4-4Q) or not;
whether the continuity of normal line directions of the edge is absent (a condition 4-5Q) or not;
whether the total value of angles of normal line directions of an edge is distant from 0° (a condition 4-6Q) or not; and/or whether the curvatures at the edge of candidate region 92 are different from each other (a condition 4-7Q) or not are judged. When the conditions 4-1Q to 4-7Q are satisfied, the candidate region 92 is judged to be actually in need of division and the processing moves to step S47.

The processing may move to step S47 either when all of the conditions 4-1Q to 4-7Q are satisfied, when any six of the conditions are satisfied, when any five of the conditions are satisfied, when any four of the conditions are satisfied, when any three of the conditions are satisfied, when any two of the conditions are satisfied, or when any one of the conditions is satisfied.

Regarding the condition 4-1Q, when the area of candidate region 92 is large (more than the certain threshold value), it is considered that a plurality of cell nuclei are detected and therefore candidate region 92 is to be divided.

Regarding the condition 4-2Q, when the circularity of candidate region 92 is low (lower than the certain threshold value) in spite of the high circularity of a general cell nucleus, it is considered that a plurality of cell nuclei are detected and therefore candidate region 92 is to be divided.

Regarding the condition 4-3Q, when a concave point is present in candidate region 92, and especially when concave points are present in positions opposite to each other, it is considered that a plurality of cell nuclei are detected and therefore candidate region 92 is to be divided.

Regarding the condition 4-4Q, when a plurality of nucleoli are present in the candidate region 92 although there is basically one nucleolus in a cell nucleus, it is considered that a plurality of cell nuclei are detected and therefore candidate region 92 is to be divided.

Regarding the condition 4-5Q, the outlines of candidate region 92 are connected and the absence of continuity of the normal line directions obtained from the connected outlines is judged, for example, the directions in the order of 0°, 90°, 180°, 270°, and 0°. If a continuity is judged to be absent, it is considered that the candidate region 92 surrounded by the outlines is to be divided.

Figure 18A:
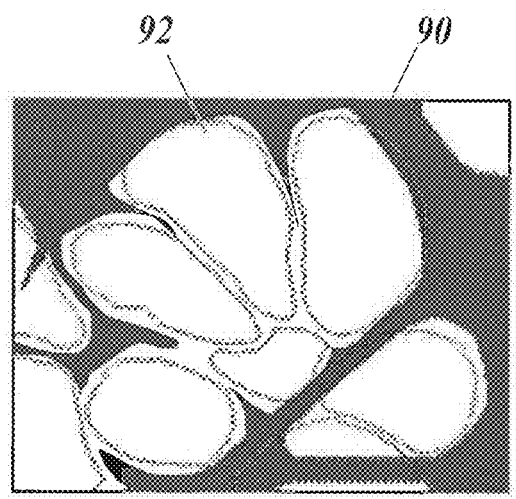
FIG. 18A is a diagram schematically explaining a presence/absence of continuity of normal line directions of an edge.
Figure 18B:
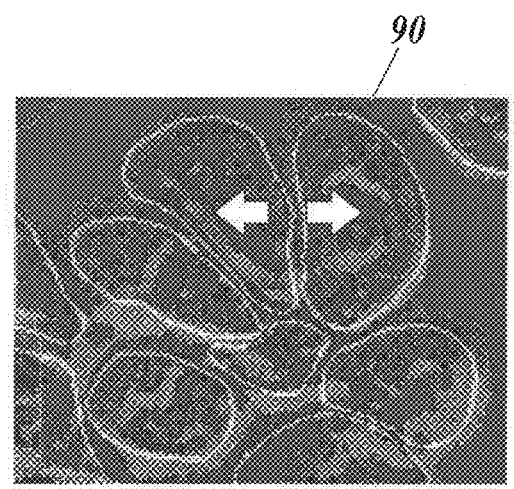
FIG. 18B is a diagram schematically explaining a presence/absence of continuity of normal line directions of an edge.

For example, as shown in FIGS. 18A to 18B, when there are normal lines having opposite directions in the image obtained by extracting normal line directions from the cell image in judging the absence of continuity of the normal line directions generated from the connected outlines of candidate region 92, it is considered that the candidate region 92 is to be divided.

Regarding the condition 4-6Q, the outline of candidate region 92 is connected and the rotation angle of the filter is changed from the range of 0° to 360° to the range of −180° to 0°, further to 180°. It is judged whether the total value of angles of normal line directions of an edge goes away from 0° by the change of the rotation angle of the filter. When the total value of angles of normal line directions of an edge goes away from 0°, it is considered that a plurality of cell nuclei are detected and therefore candidate region 92 to be divided.

Regarding the condition 4-7Q, when the curvatures at the edge of candidate region 92 are different from each other, it is considered that a plurality of cell nuclei are detected and therefore candidate region 92 is to be divided.

Figure 17B:
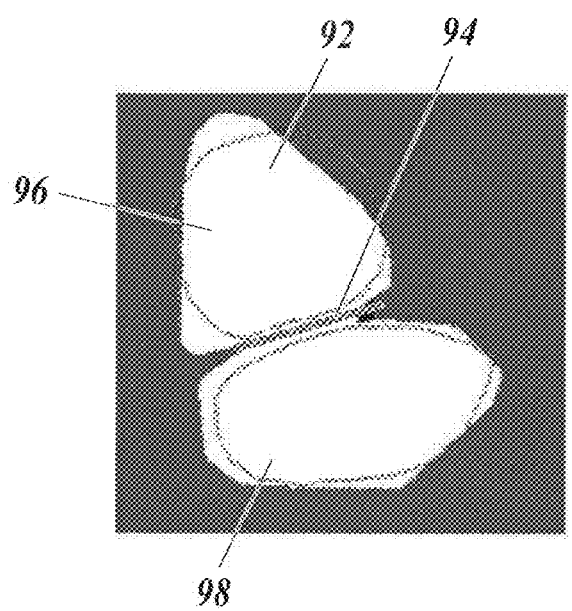
FIG. 17B is a diagram schematically explaining one of the processes, from judging processing to judge whether a candidate region of a cell nucleus needs to be divided or not to division processing to divide the candidate region of cell nucleus.

In step S47, as shown in FIG.17B, a boundary line 94 for dividing candidate region 92 (a dividing pattern) is searched, and candidate region 92 is divided into region 96 and region 98 by the boundary line 94.

Subsequently, the regions 96 and 98 are determined whether to satisfy the following conditions similar to the conditions 4-1Q to 4-7Q (step S48);

whether the areas of candidate regions 96 and 98 are within a certain threshold value (a condition 4-1A) or not;

whether the circularities of candidate regions 96 and 98 are equal to or more than a certain threshold value (a condition 4-2A) or not;

whether a concave point is absent in the candidate regions 96 and 98 (a condition 4-3A) or not;

whether a plurality of nucleoli are absent in the candidate regions 96 and 98 (a condition 4-4A) or not;

whether the continuity of normal line directions of the edge is absent (a condition 4-5A) or not;

whether the total value of angles of normal line directions of an edge is within a certain range from 0° (a condition 4-6A) or not; and/or whether the difference between the curvatures at the edge of candidate regions 82a to 82c becomes smaller and is within a certain range (a condition 4-7A) or not.

When the conditions 4-1A to 4-7A are satisfied, division processing of the candidate region 92 is performed (step S49).

The processing may move from step S48 to step S49 either when all of the conditions 4-1A to 4-7A are satisfied, when any six of the conditions are satisfied, when any five of the conditions are satisfied, when any satisfied, when any four of the conditions are three of the conditions are satisfied, when any two of the conditions are satisfied, or when any one of the conditions is satisfied.

Figure 17C:
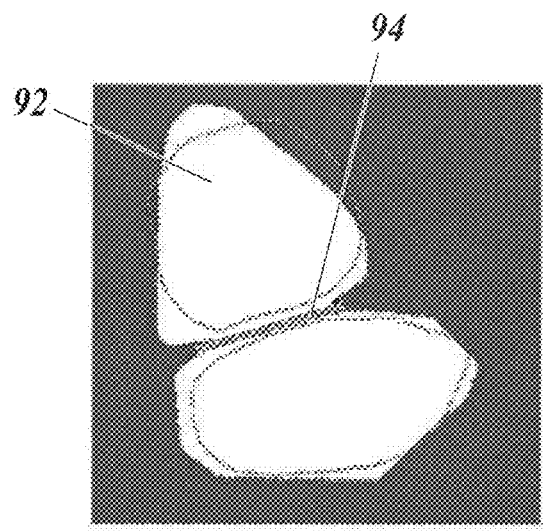
FIG. 17C is a diagram schematically explaining one of the processes, from judging processing to judge whether a candidate region of a cell nucleus needs to be divided or not to division processing to divide the candidate region of cell nucleus.
Figure 17D:
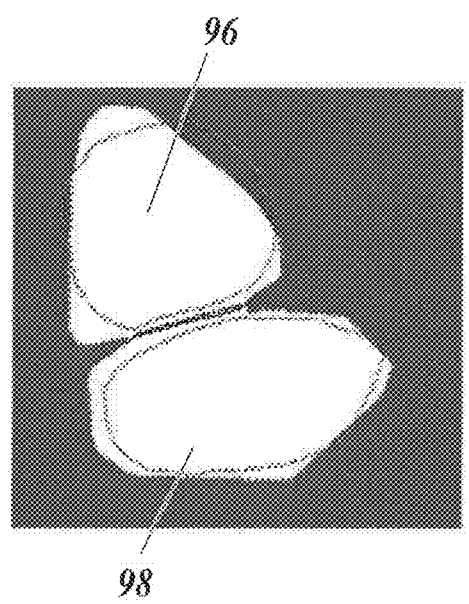
FIG. 17D is a diagram schematically explaining one of the processes, from judging processing to judge whether a candidate region of a cell nucleus needs to be divided or not to division processing to divide the candidate region of cell nucleus.

In step S49, as shown in FIGS. 17C to 17D, candidate region 92 is divided into region 96 and region 98 by boundary line 94.

Figure 19:
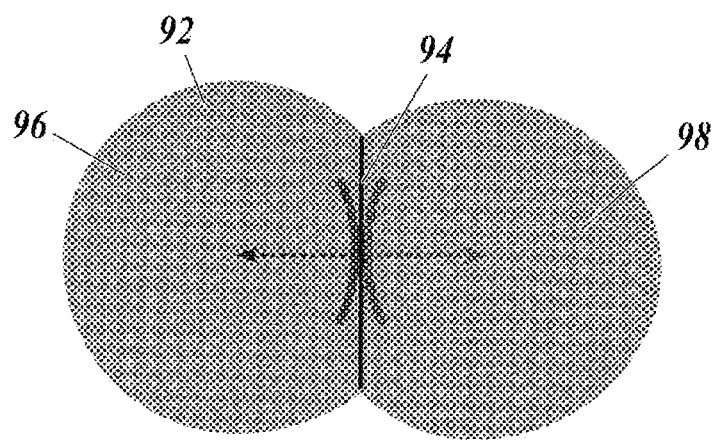
FIG. 19 is an example of division processing of a candidate region of cell nucleus.

Specifically, in steps S47 and S49, as shown in FIG. 19, candidate region 92 is divided into region 96 and region 98 using boundary line 94 which is set between edge portions having high edge intensity, in the image generated by extracting edge intensity from the cell image.

In the image generated by extracting normal line directions of edge from the cell image, candidate region 92 may be divided into region 96 and region 98 using boundary line 94 which is set between the portions whose normal line directions are opposite to each other.

Candidate region 92 may be divided into region 96 and region 98 using boundary line 94 which is set between concave points in candidate region 92 according to publically-known methods (Bottle-Neck: see Pattern Recognition, Volume 45, Issue 7, Pages 2780-2787 (July 2012)).

Candidate region 92 may be divided into region 96 and region 98 using boundary line 94 set in candidate region 92 according to a publically-known watershed method.

Finally, as shown in FIG. 3, a processing is performed to detect the integrated region (84) or each of the divided regions (96 and 98) as a single nucleus (step S50).

According to the present embodiment shown above, whether to correct the candidate regions of a cell nucleus or not is judged in step S41 on the basis of region information of cell nucleus. Further, the candidate regions are integrated based on a judgement of whether to integrate the candidate regions of a cell nucleus or not on the basis of region information of cell nucleus and edge information of cell nucleus in steps S42 to S45, or the candidate regions are divided based on a judgement of whether to divide the candidate region of cell nucleus or not on the basis of region information of cell nucleus and edge information of cell nucleus in steps S46 to S49. Accordingly, an individual cell nucleus can be detected without incorrectly detecting a single cell nucleus as a plurality of cell nucleus, even when the cell nucleus is not stained uniformly or is contiguous with neighboring cell nuclei.

The description of the embodiment is a suitable example of the present invention, and the present invention is not limited to them.

For example, according to the embodiment, a tissue slice of a human body is described as the object of the pathological diagnosis. The tissue includes tissue culture and can be replaced with separated cells from the tissue or cultured cells.

The above description discloses an example which uses an HDD, a semiconductor nonvolatile memory, or the like as the computer readable medium of the program of the present invention, however, the present invention is not limited to the above. A portable recording medium such as a CD-ROM, etc. can be applied as other computer readable media. A carrier wave can be applied as the medium which provides the data of the program of the present invention through a communication line.

Other than the above, the detailed configuration and the detailed operation of each device composing the pathological diagnosis assistance system 10 can be suitably changed within the scope of the present invention.

INDUSTRIAL APPLICABILITY

The present invention can be used in the field of image processing for pathological diagnosis.

REFERENCE NUMERALS 1A microscopic image obtaining apparatus
2A image processing device
3A cable
10 pathological diagnosis assistance system
21 control section
22 operation section
23 display section
24 communication I/F
25 storage section
26 bus
30, 40, 50 cell image
82a to 82f candidate region of cell nucleus (before integration)
84 region after integration
92 candidate region of cell nucleus (before division)
96, 98 region after division

The invention claimed is:

1. An image processing device for detecting a cell nucleus in a cell image in which the cell nucleus is stained, comprising:
a region-extracting unit to extract a candidate region and region information of the cell nucleus from the cell image;
an edge-extracting unit to extract an edge information of the cell nucleus from the cell image;
a judging unit to judge whether to integrate a plurality of the candidate regions or to divide one of the candidate regions, on the basis of the region information of the cell nucleus and the edge information of the cell nucleus; and
a correcting unit to correct the candidate region of the cell nucleus on the basis of a judgement result by the judging unit and to detect the cell nucleus.

2. The image processing device according to claim 1, wherein the edge information includes at least one of edge intensity, edge angle, normal line direction of an edge, and curvature at an edge.

3. The image processing device according to claim 1, wherein the judging unit
calculates or detects at least one of area, circularity, presence of a concave point, and presence of a nucleolus in the candidate region of the cell nucleus, on the basis of the region information of the cell nucleus;
calculates or detects at least one of presence of continuity of normal line directions of an edge, total value of angles of normal line directions of an edge, and curvature at an edge, on the basis of the edge information of the cell nucleus; and
judges whether to integrate a plurality of the candidate regions of the cell nucleus or to divide one of the candidate regions of the cell nucleus, on the basis of the calculated or detected results.

4. The image processing device according to claim 3, wherein the correcting unit integrates a plurality of the candidate regions of a cell nucleus on the basis of at least one of
calculated result of area of the candidate regions of a cell nucleus;
calculated result of circularity of the candidate regions of the cell nucleus;
calculated or detected result of presence of continuity of normal line directions of an edge;
calculated or detected result of total value of angles of normal line directions of an edge; and
calculated or detected result of curvature at an edge.

5. The image processing device according to claim 3, wherein the correcting unit divides one of the candidate regions on the basis of at least one of calculated or detected results of
area of candidate region of the cell nucleus;
circularity of candidate region of a cell nucleus;
presence of a concave point in the candidate region of the cell nucleus;
presence of a nucleolus in the candidate region of the cell nucleus;
presence of continuity of normal line directions of the edge;
total value of angles of normal line directions of an edge; and
curvature at the edge.

6. A non-transitory computer-readable storage medium including an image processing program for controlling a computer for detecting a cell nucleus in a cell image in which the cell nucleus is stained to function as:
a region-extracting unit to extract a candidate region and region information of the cell nucleus from the cell image;
an edge-extracting unit to extract an edge information of the cell nucleus from the cell image;
a judging unit to judge whether to integrate a plurality of the candidate regions or to divide one of the candidate regions, on the basis of the region information of the cell nucleus and the edge information of the cell nucleus; and
a correcting unit to correct the candidate region of the cell nucleus on the basis of a judgment result by the judging unit and to detect the cell nucleus.

* * * * *